(12) United States Patent (10) Patent No.: US 8,346,368 B2
Killian (45) Date of Patent: Jan. 1, 2013

(54) SOUND PROCESSING METHOD AND SYSTEM

(75) Inventor: Matthijs J. P. Killian, Mechelen (BE)

(73) Assignee: Cochlear Limited, NSW (AU)

( * ) Notice: Subject to any disclaimer, the term of this patent is extended or adjusted under 35 U.S.C. 154(b) by 116 days.

(21) Appl. No.: 12/995,395

(22) PCT Filed: Apr. 17, 2009

(86) PCT No.: PCT/AU2009/000482
§ 371 (c)(1),
(2), (4) Date: Nov. 30, 2010

(87) PCT Pub. No.: WO2009/143553
PCT Pub. Date: Dec. 3, 2009

(65) Prior Publication Data
US 2011/0077712 A1 Mar. 31, 2011

(30) Foreign Application Priority Data
May 30, 2008 (AU) ................................ 2008902738

(51) Int. Cl.
*A61N 1/36* (2006.01)
(52) U.S. Cl. .............. 607/57; 607/55; 607/56; 607/136; 607/137
(58) Field of Classification Search .............. 607/55–57, 607/136–137
See application file for complete search history.

(56) References Cited

U.S. PATENT DOCUMENTS
6,205,360 B1 3/2001 Carter et al.
6,240,192 B1 5/2001 Brennan et al.
7,953,490 B1 * 5/2011 Fridman .......................... 607/57

OTHER PUBLICATIONS

Chatterjee, et al., "Effects of phase duration and electrode separation on loudness growth in cochlear implant listeners", J. Acoust. Soc. Am. 2000 Mar. 2000, pp. 1637-1644.
Chatterjee, Monita "Effects of stimulation mode on threshold and loudness growth in multielectrode cochlear implants", J. Accoust. Soc. Am., 2000 Feb. 1999 , pp. 850-860.
Fu, Qian-Jie "Loudness growth in cochlear implants: effect of stimulation rate and electrode configuration", Hearing Research 2005 , 55-62.
International Search Report of PCT/AU2009/000482, mailed Jul. 20, 2009, 6 pages.
Written Opinion, "PCT/AU2009/000482", mailed Jul. 20, 2009, 8 pages.

* cited by examiner

*Primary Examiner* — Carl H Layno
*Assistant Examiner* — Paula J Stice
(74) *Attorney, Agent, or Firm* — Kilpatrick, Townsend & Stockton, LLP.

(57) ABSTRACT

Coding of received audio signals and the resulting application of electrical stimuli applied to electrodes used in a cochlear implant system are disclosed together with a method of fitting this new coding strategy. One of the aims is to improve place specific stimulation representing pitch by applying near threshold electrical stimuli with limited and focused excitation fields. A range of stimulation rates and a minimal range of current levels above threshold are used for creation of a dynamic loudness percept for a cochlear implant recipient. Another aim is to disclose a coding scheme based on a model of physiological measures (i.e. refractoriness, adaptation, spread of activation field, spatiotemporal acoustical cochlear activation patterns and spontaneous activity) to estimate the proportions of available excitable auditory neurons close to the electrodes available for stimulation. The spectral bands formed from the pre-processing of incoming audio signals are weighted by these proportions of excitability to control place, timing, rate and current level of electrical stimuli applied to the electrodes available in the array.

20 Claims, 18 Drawing Sheets

*Fig. 24*

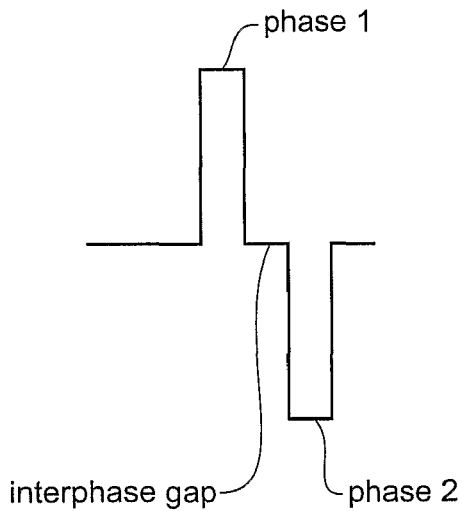
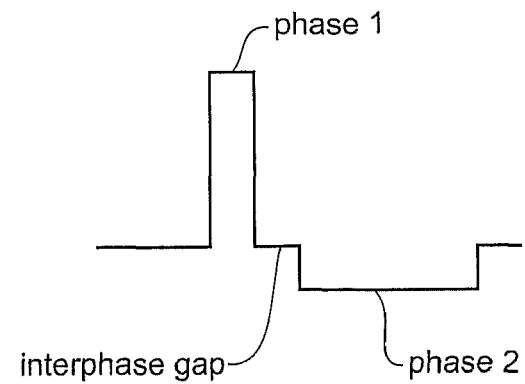
*Fig 37a*
*Fig 37b*
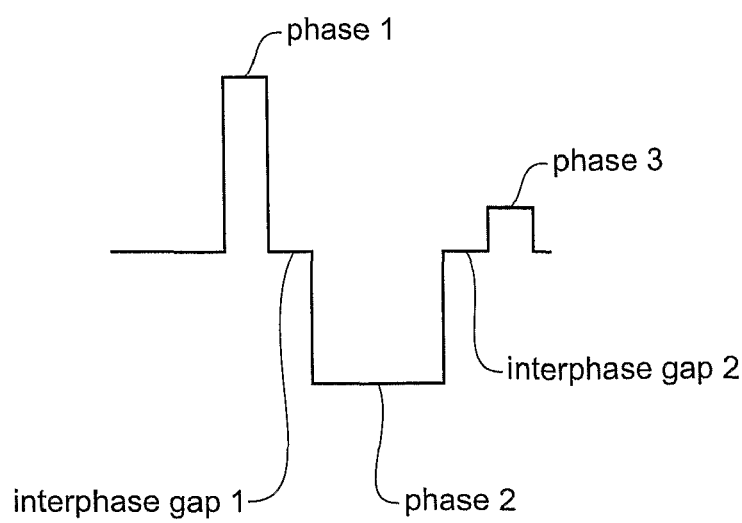
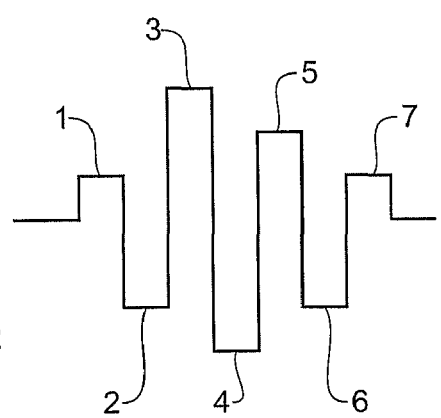
*Fig 37c*
*Fig 37d*

SOUND PROCESSING METHOD AND SYSTEM

CROSS-REFERENCE TO RELATED APPLICATION

The present application is a National Stage application of PCT/AU2009/000482 entitled "Sound Processing Method and System", filed on May 30, 2009, which claims priority from Australian Provisional Patent Application No. 2008902738, filed on May 30, 2008, which are hereby incorporated by reference herein.

BACKGROUND

1. Field of the Invention

This invention relates to generally to cochlear implants, and more particularly to applying stimulation.

2. Related Art

Sound vibrations that impinge on the outer and middle ear of a person with normal hearing, are conveyed to a tiny shell-like organ called the cochlea where they are spatially dispersed according to their frequency across a vast number of available excitable auditory neurons of the spiral ganglion. Profound deafness often arises when outer, middle or inner ear vibration pathways are severed or when the neural and/or sensory hair cells of the cochlea are damaged.

Implanted hearing prostheses that stimulate the inner ear can be used to assist people with total or partial hearing loss. In general, such devices employ electronic analogue and digital techniques to process, and transform received sound or signals representing sound, into one or more discrete channels of mechanical and/or electrical stimulus information. The resulting stimulus is then conveyed to auditory neurons within the recipient's cochlea associated with the sense of hearing through the central auditory pathways. In this way, persons with severe to profound hearing loss are able to perceive a potentially beneficial approximation of sound. The use of an array of electrodes which are surgically implanted in the recipient's cochlea results in an implant that is unique in every recipient since the final resting place of each electrode is unique to the recipient and the particular spatial distribution of auditory neurons within the recipient's cochlea. The fitting of a coding strategy in a recipient with an implanted hearing prostheses aims to give the individual patient the maximal benefit of the available coding options.

The fidelity of sound perceived by the recipient of an implanted hearing prosthesis is greatly affected by their ability to distinguish pitch and loudness which is severely limited by the relatively small number of discrete electrodes (say 20 or so) which can be fitted within the narrow confines of their cochlea and which are intended to stimulate the available auditory neurons (some 20,000-40,000). The dispersal along the cochlea of applied electrical stimulation to a single electrode further conspires to degrade the recipient's ability to discriminate sounds that are close in frequency. The above processes are further complicated by the need to stimulate multiple electrodes at the same time or at close intervals to better mimic the received audio.

As a consequence, most recipients have difficulty with recognition, perception and appreciation of environmental sounds, speech in noise and music.

Electrical stimulation of the cochlea complicates perception of sound particularly speech in noise and music for the recipient and thereby limits their ability to learn and adapt to their newly acquired prosthetic hearing. This is especially relevant when the recipient is an infant or person with little or no prior experience of sound and its relationship to everyday events. Currently the process of learning to use an implanted hearing prosthesis requires extensive and long-term habilitation provided by health care professionals after the particular physical characteristics of the recipient's cochlear implant are tested and incorporated into the way in which simulation signals are applied to one or more electrodes.

There exist a number of coding schemes and stimulation methods all of which use a combination of current pulses of varying rate and intensity to provide a sensation to the cochlear implant recipient that matches respectively the received pitch (frequency) and loudness of the often quite complex received sound, all with limitations and characteristics that the recipient then lives with or copes with to the limit of their ability and the coding and signaling capability of the implant and its associated audio and signal processing devices.

SUMMARY

In accordance with a first aspect of the present invention, there is provided a method for delivering a stimulation by a cochlear implant having a plurality of electrodes, comprising: receiving a sound signal; filtering the received signal to obtain a set of one or more band limited signals each corresponding to a particular frequency band; applying a weight to at least one of the band limited signals to obtain at least one weighted signal, wherein the applied weight is determined using a function of the excitability of neurons in the vicinity of at least one electrode of the plurality of electrodes corresponding to the frequency band of the band limited signal; selecting a signal from amongst the weighted signals; generating a stimulation signal based on the selected signal; and delivering the stimulation signal via at least one of the electrodes.

In accordance with a second aspect of the present invention, there is provided a cochlear implant comprising: a microphone; a plurality of electrodes; and a signal processor configured to filter a sound signal received from the microphone to obtain a set of one or more band limited signals each corresponding to a particular frequency band, apply a weight to at least one of the band limited signals to obtain at least one weighted signal, wherein the applied weight is determined using a function of the excitability of neurons in the vicinity of at least one electrode of the plurality of electrodes corresponding to the frequency band of the band limited signal, select a signal from amongst the weighted signals, generate a stimulation signal based on the selected signal, and deliver the stimulation signal via at least one of the electrodes.

BRIEF DESCRIPTION OF THE DRAWINGS

FIG. 4a depicts a bipolar+1 stimulation mode;

FIG. 4a depicts a monopolar stimulation mode;

FIG. 4b depicts a bipolar+1 simulation mode;

FIG. 24 depicts a model used to calculate the excitability of the neurons associated with an electrode array;

FIGS. 37a shows biphasic symmetrical current pulses with an inter-phase-gap;

FIGS. 37b shows asymmetrical biphasic current pulses;

FIGS. 37c shows triphasic current pulses including a variety of phase durations; and FIGS. 37d shows pulses containing more than 3 phases (for example 7 phases).

DETAILED DESCRIPTION

Within this description the term nerve fibre and other terms such as auditory neuron/spiral ganglion neuron/auditory nerve fibre are to be considered equivalents for the purposes herein and most commonly the term neurons will be used to represent the above features of the cochlea region of the human body.

Figure 1:
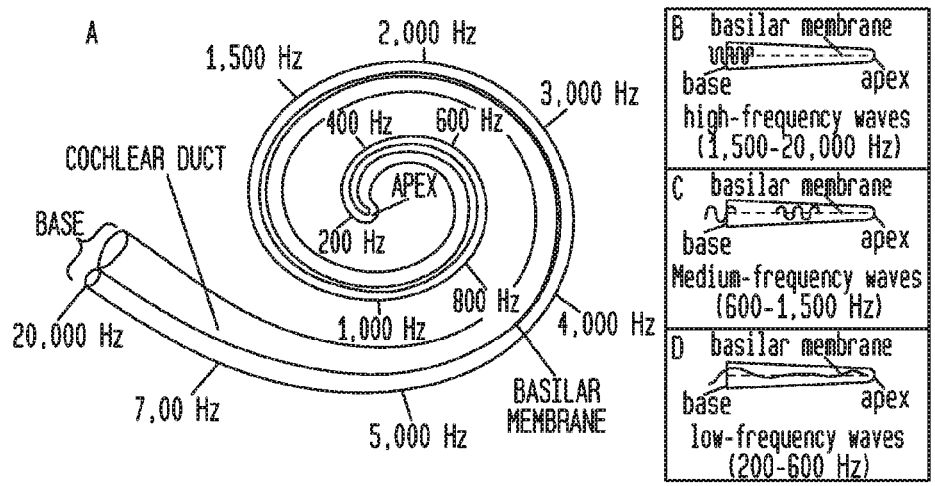
FIG. 1A depicts the cochlea and the frequencies that are detected by different parts of the cochlea are identified.
FIGS. 1B, C and D depict the travelling wave of sound along the cochlea aquaduct.

By way of example FIG. 1 depicts a cochlea and the frequencies that are detected by different parts of the cochlea are identified. It will be noted that the higher frequencies are detected by the apical part of the cochlea and the lower frequencies are detected by the basal part of the cochlea.

Figure 2:
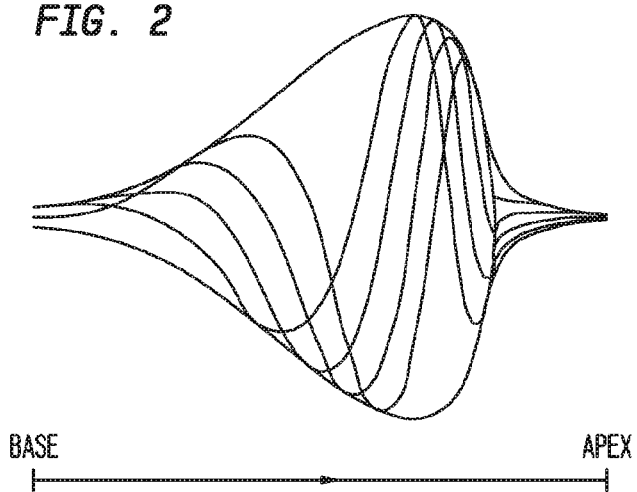
FIG. 2 depicts the travelling wave concept along the cochlea aqueduct.

FIG. 2 depicts a travelling wave concept along the cochlea aqueduct. Temporal aspects can be introduced into the disclosed coding strategy by temporal weighting of the excitability along the electrode array based on spectral phase delays/shifts and the travelling wave concept known from the physiological, biophysical and psychophysical literature.

Figure 3:
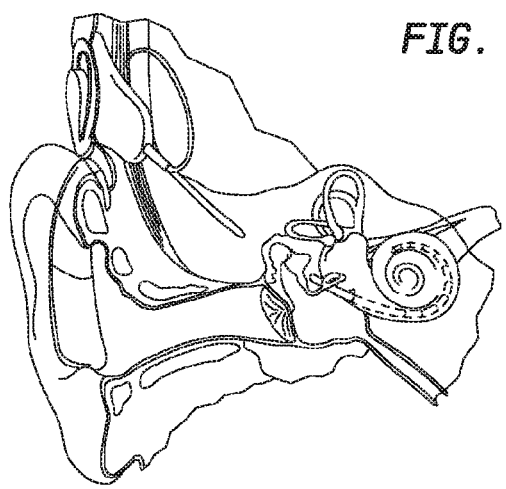
FIG. 3 depicts a cochlear implant system with an array of perimodiolar electrodes implanted in a cochlea.
Figure 4A:
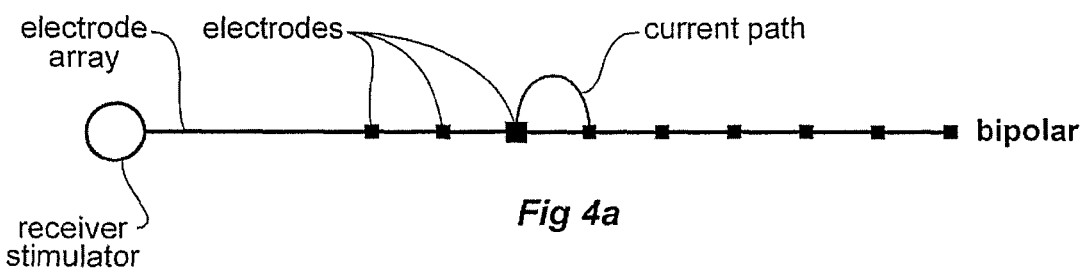
FIG. 4a depicts a bipolar stimulation mode, in accordance with an embodiment of the present invention
Figure 4B:
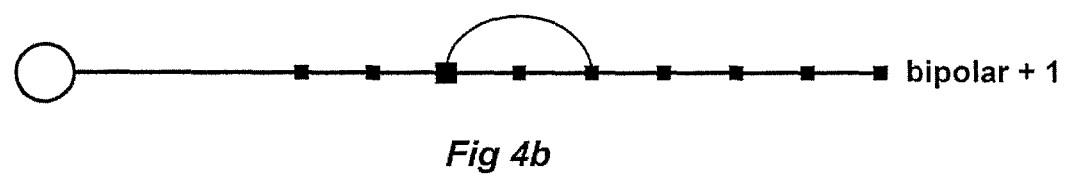
FIG. 4b depicts a bipolar+2 stimulation mode.
Figure 4C:
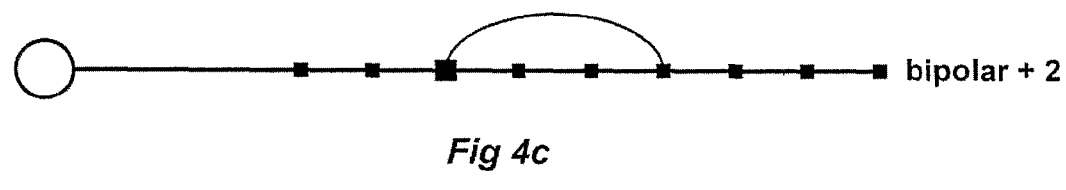
FIG. 4c depicts a bipolar+2 simulation mode.
Figure 4D:
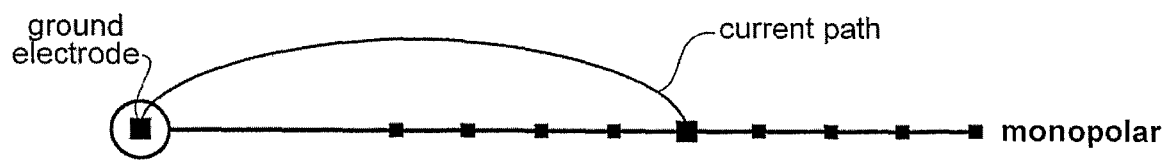
FIG. 4d depicts a monopolar simulation mode.
Figure 4E:
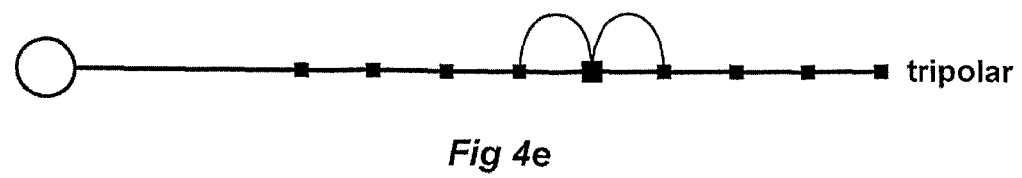
FIG. 4e depicts a tripolar simulation mode.
Figure 4F:
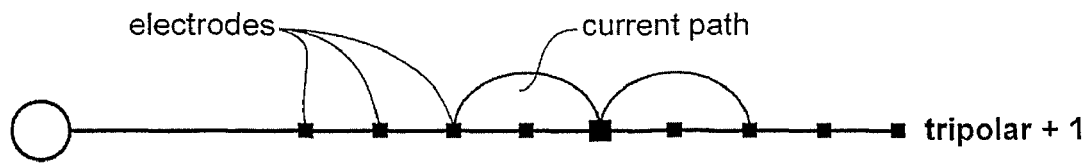
FIG. 4f depicts a tripolar+1 simulation mode.
Figure 4G:
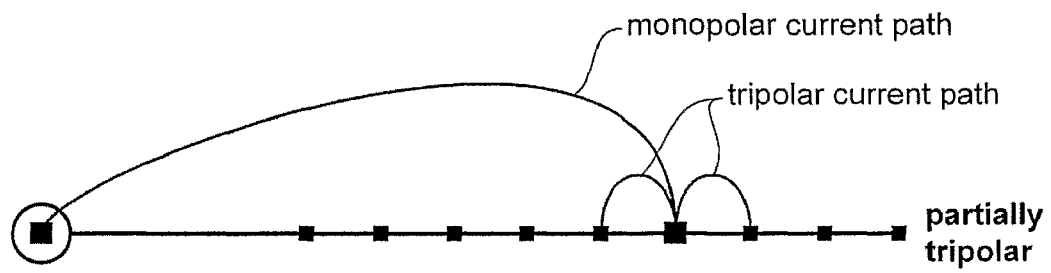
FIG. 4g depicts a partially tripolar simulation mode.
Figure 4H:
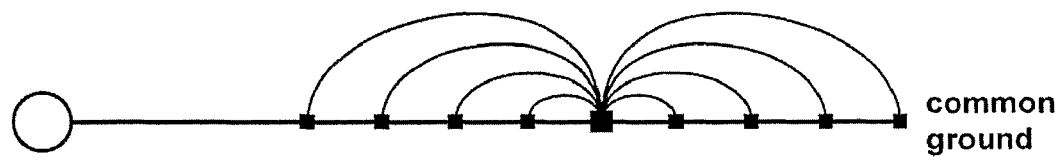
FIG. 4h depicts a common ground simulation mode.
Figure 4I:
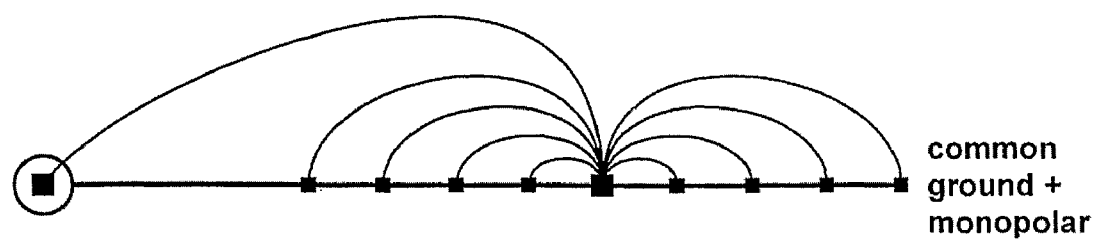
FIG. 4i depicts a common ground+monopolar simulation mode.
Figure 4J:
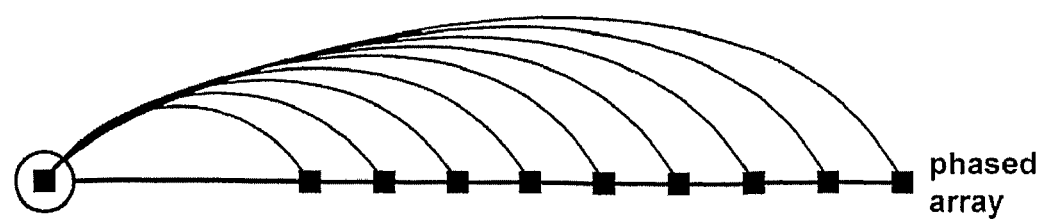
FIG. 4j depicts a phased array simulation mode.
Figure 4K:
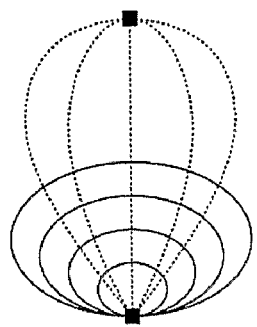
FIG. 4L depicts current fields and potential fields during bi-polar stimulation.
FIG. 4m depicts current fields and potential fields during common ground stimulation.
FIG. 4n depicts current fields and potential fields during tri-polar (4m) stimulation.
Figure 4L:
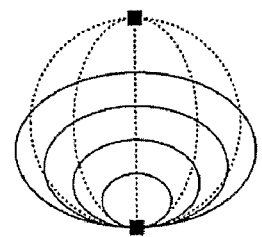
Figure 4M:
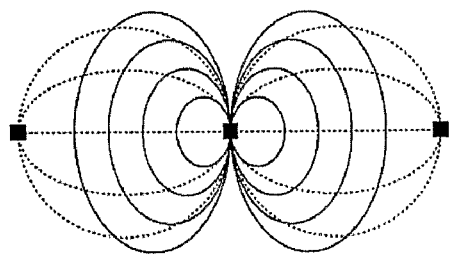
Figure 4N:
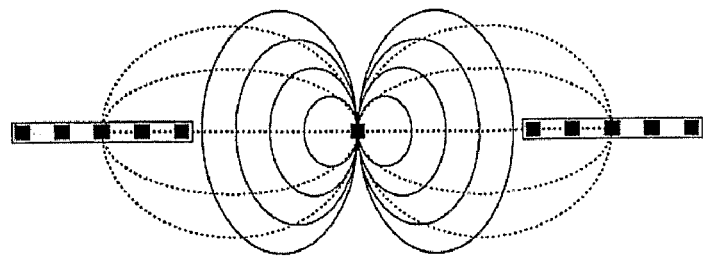

FIG. 3 depicts a cochlear implant system with an array of perimodiolar electrodes implanted in a cochlea. Perimodiolar placement puts the electrode contacts in close vicinity to the auditory neurons in the spiral ganglion to better focus stimulation of the frequency regions indicated in FIG. 1. An embodiment disclosed herein aims to make maximal use of the focused stimulation of perimodiolar electrodes and potentially allows for further improvements in performance with multi-electrode arrays with more than 20 focused channels.

When applying electric current through one of the electrodes in the array, the current also passes into the region adjacent the electrode and when electrodes are close by the applied current from adjacent electrodes can enter regions adjacent other electrodes. Stimulation along the tonotopy of the cochlea of auditory neurons aims to replicate the stimulation that would occur in a normally functioning cochlea. However, it can never be exactly the same since there is no mechanical or electromechanical replacement at this time for the thousands of tiny hairs that line the cochlea which are responsible for the translation of vibratory sound energy into electrical stimulation of the many tens of thousands of auditory neurons. Increasing the number of electrodes is a worthy long term aim but not practical at this time.

Surgeons use their skill to place all of the electrodes of an array in close contact with the full length of the spiral ganglion and adjacent to the location of the auditory neurons, ensuring at the same time that the placement will be stable over the lifetime of the recipient.

A multi-electrode array when appropriately stimulated is used to excite many auditory neurons simultaneously or at least in a manner which mimics their natural state as if the received audio was received in a healthy cochlea.

It is known that a way to improve this arrangement may involve:
1. perimodiolar placement of the electrode array; and
2. use of stimuli that causes narrow excitation fields: e.g. tri-polar stimulus (Common Ground involving three adjacent electrodes) or phased array stimulation (the stimulation field is focussed by balancing of the currents at all electrodes in the array according to a model predicting the current fields close to the neural elements).

FIGS. 4a to 4j depict a linear array of electrodes and illustratively the current path between electrodes for different modes of stimulation. These include bipolar (4a), bipolar+1 (4b), bipolar+2 (4c), monopolar (4d), tripolar (4e), tripolar +1 (4f), partial tripolar (4g), common ground (4h), common ground+monopolar (4i) and phased array (4j). Of course it will be understood that any other type of suitable stimulation mode may also be used.

It will also be understood that the term "partial tripolar" may also sometimes be referred to or known as "quadrupolar". In partial tripolar, or quadrupolar, use is made of 1 active electrode and 3 return electrodes. In one arrangement, half the current returned may be returned to the extracochlea reference electrode (the ground electrode in FIGS. 4a to 4j) and the other half of the returned current is returned to 2 electrodes apically and basally of the active electrode. Other current distributions may also be used, for example 75% to the reference electrode and 25% to the apical and basal electrodes.

FIGS. 4k to 4n also depict the current paths (dotted lines) and potential fields (solid lines) during mono-polar 4k (electrodes well spaced), bi-polar 4l, tri-polar 4m and common ground 4n stimulation which relate to closely spaced electrodes. Tri-polar stimulation 4m is much the same as common ground stimulation 4e and includes the use of only 3 adjacent electrodes.

Phased array stimulation includes matrix calculation of the electrical field during ensemble simultaneous electrode activity to control stimulation in such a way that the electrical stimulation fields occur at desired place within the cochlea and thereby activate the desired auditory neurons. It is an advanced means to create focused stimulation. However, it is known that in all the mentioned stimulation modes an increase in the current level is applied to increase the perceived loudness, but that this approach also results in spatial broadening of the excitation field about the respective electrode/s to which the current is applied. This has the effect of spreading the tonal signal perceived amongst the excitable neurons and this has the undesirable effect of broadening the spectrum of the perceived audio signal. Using an analogy, due to the dispersed excitation field caused by the use of greater current levels to create higher loudness, a pure tone audio signal that is desired to be mimicked at a desired loudness is not perceived as a single tone by a cochlear implant recipient.

There are many schemes available which aim to improve the fidelity of the mimicry including the preprocessing of the received audio signal to break up the signal into as many bands as there are electrodes and application of a signal to a respective electrode at a current that is proportional to the peak sound pressure level received in that band. The correlation between loudness and current level is not exactly proportional since the position of a sensor and the effectiveness of current delivery is variable between recipients but those characteristics can be mapped for each recipient following appropriate testing (the resulting information is referred to as a MAP). The mapping becomes more complicated as there will be a spread of the zone of excitation caused by large currents delivered to adjacent regions where other electrodes are being stimulated at the same time, when complicated and quickly varying received audio signals are processed, merely using a proportional approach leads to overly loud and blunt perception without spectral contrast when compared to the physiological and biophysical information processing within the normal acoustically stimulated ear.

An exemplary embodiment of the present invention seeks to minimize the excitation field applied to a single electrode by only using (or using just as much as possible) a near threshold current to stimulate each electrode in an array.

Different stimulation modes can still be applied and used in combination in the embodiment. These stimulation modes may include:
a) Bi-polar stimulation: mono-polar, bi-polar, tri-polar, partially tri-polar, common ground and phased array stimulation
   a. Stimulation levels can be adapted by change of current level, Inter Phase gaps (IPG) and pulse widths
b) Pulse trains:
   a. Stimulation levels can be adapted by change of pulse train stimulation rate and duration wherein different pulse train functions combined over multiple electrodes can be applied.
c) Short oscillatory bursts of square, triangular and sine wave
d) Sequential stimulation of electrodes to avoid channel interaction of the current fields
e) Simultaneous stimulation of electrodes
   a. Simultaneous stimulation of paired electrodes can be used to create virtual pitch channels; by use of near threshold stimuli these virtual channels can be fully exploited and are expected to truly increase the spectral resolution available for cochlear implant recipients.
   b. Simultaneous stimulation of non overlapping current and/or excitation fields can be used to increase the overall rate without the disadvantage of channel interaction.

It is however not as simple as applying just enough current to an electrode to mimic a frequency stimulation as the recipient also needs to determine the loudness of the received audio signal (useful in determining location as well as adding the supple nuances of language and music).

The presently described embodiment recognizes that cochlear implant users primarily use changes in the spectral envelope of received audio signals for categorizing their listening experience. The new coding strategy herein disclosed, in one form, seeks to achieve optimal mimicry of the changes in the spectral envelope in the auditory neuron activity which has to be tonotopically organized along the spiral ganglion of the cochlea using the available implanted electrodes.

As described previously, conventional coding strategies use a dynamic loudness range that is created by determining a range of current levels between a threshold (T) and comfort (C) level as perceived by the recipient. C level is also known as Most Acceptable Level (MAL). In general the higher the current level the higher the loudness. These levels are obtained for each electrode in the array to create what is termed a T profile and a C profile along the electrode array. If one uses these profiles for a MAP, the MAP often sounds too loud as loudness is summed by the auditory neurons when more that one electrode is activated in close succession (or simultaneously). Therefore the C-profile is often lowered to create a comfortable MAP for a recipient. If one creates a MAP with a narrow dynamic range of say 1 current level based on the T-profile one can still lower the whole MAP and obtain a perceptible loudness when all electrodes are activated in close succession (or simultaneously).

Figure 5:
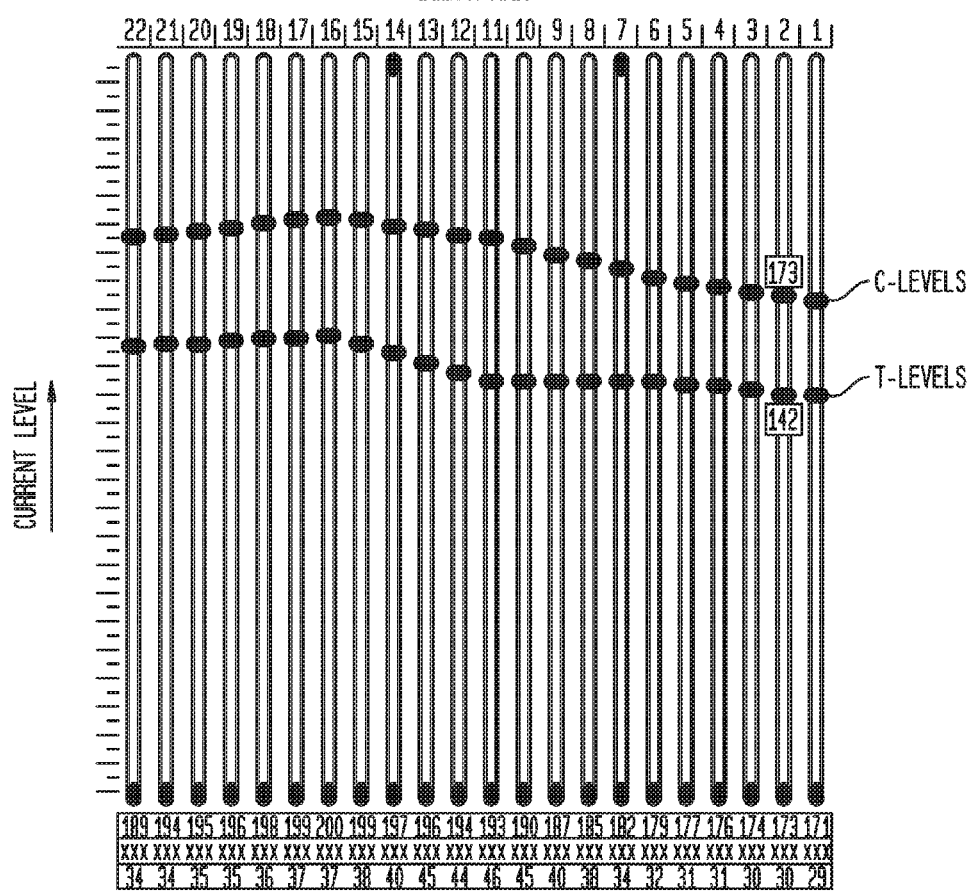

FIG. 5 is an example MAP created with custom software for a recipient and would be used in conventional coding to indicate the Threshold (T) and Comfort (C) Current Levels for 22 electrodes that encompass the Dynamic Range (DR) of Current Level (CL) on which the loudness of the incoming sound is projected to create an acceptable loudness for the recipient of the implant.

The horizontal arrays from top to bottom display the: electrode number, comfort level (C), threshold level (T), dynamic range (DR)=C−T; and on the vertical axis Current Level; the black dots represent the T levels and the grey dots represent the C levels of a MAP.

Cochlear implant users can perceive the rate of stimulation when they are stimulated at very low rates. For example, they tend to hear a galop when stimulated on a single electrode at a rate of 100 pulses per second. Increases in the rate of stimulation on a single electrode yield changes along different perceptual dimensions until the rate is increased beyond a given critical rate, after which changes in rate are only perceived as changes in loudness. The critical rate beyond which a rate increase no longer elicits changes in perceptual dimensions other than loudness is in most subjects approximately 300 Hz.

The inventor has determined that increasing the rate of stimulation beyond the critical rate (about 1000 pulses per second) would eventually result in changes of perception (other than loudness.) Our data replicate the previously observed results that rates between approximately 300 and 1000 Hz create a singular pitch percept.

The inventor has determined that applying pulses of current within a range of rates to one electrode but at the T level, will result in not only a perception of tone but also loudness of that tone. Thus, the rate of current pulse delivery can be used to code for loudness while focusing the stimulation on the available auditory neurons in the vicinity of the electrode.

The coding strategy can also make use of stimulation rate in combination with current levels for coding of loudness. This will particularly helpful for electrode arrays with limited number of electrodes.

The resolution of the spectral representation in the auditory nerve activity is limited by the number of electrodes incorporated in the intra-cochlear electrode. The resolution can be increased by increasing the number of electrodes in the array.

It is anticipated that the more electrodes available the more effective the coding strategy. Ideally a singular psychophysical dimension resembling pitch is perceived by the recipient when one electrode (or channel) is stimulated at the range of rates used for coding of loudness. The effective range is expected to lie between 300-1000 pulses per second but will vary amongst implant recipients, the number of implanted electrodes, and the type of current stimulation mode.

Loudness is coded using rate distributed over the input dynamic range with the lowest rate at threshold-level and the highest rate at a comfortable-level. Rates are used commensurate to the received sound level of a frequency band (channel) determined to be most applicable to the spatial location of a respective electrode, and stimuli are applied to the electrode at an update rate that allows maximal stimulation rate for each channel. For sequential stimulation the maximal total stimulation rate can be calculated by summing the highest rates allocated to the electrodes available in the array. E.g. for an implant with 20 electrodes the total rate needed is 20*1000=20.000 pps. The total stimulation rate for sequential stimulation is limited by the pulse widths and the inter phase gaps of the stimulus pulse, and also the RF coding schemes. If needed (e.g. for electrode arrays with more than 22 channels) the total stimulation rate can be enhanced by use of simultaneous stimulation of channels with non-interfering current fields (or phased array stimulation).

The coding strategy disclosed herein makes use of near threshold stimuli and the lowest loudness is generated by the lowest rate. The lowest rate also needs the highest current level to generate a threshold. This seems a paradox. The solution is that during the testing that is undertaken once the implant is surgically implanted in the recipient, it is possible to measure a psychophysical threshold current level profile using a high rate pulse train then use this current level profile for all rates. To be sure that there is a sensation at the lowest stimulation rate: the current level profile for the lowest rate (i.e. about 300 pulses per second (pps)) can be increased by shifting the profile with a narrow dynamic current level range upwards during random continuous low rate stimulation until a psychophysical threshold for the overall stimulation is found. One might expect that the absolute upward shift in current levels depends on the number of electrodes in the array and the higher the number of electrodes the less the shift. It is expected that in clinical practice the Threshold Current Level used by the recipient will be between the high rate profile and the low rate profile and will depend on the number of active electrodes and the neural survival in the spiral ganglion.

As alternative for the psychophysical threshold current level profile one can make use of a threshold profile obtained through objective neurophysiological measures like electrically evoked compound action potentials of the auditory nerve (ECAP) measured through telemetry (NRT) or electrically evoked brainstem potentials (EABR).

FIG. 6 schematically depicts the reason there is an absolute downward shift in current levels that depends on the number of electrodes in the array and that the higher the number of electrodes the more the shift.

An auditory neuron contains a dendrite (which runs to the hair cells) and a neurite or axon that runs in the modiolus. In a normal ear one can stimulate the dendrite, cell body, axon and/or hair cells. In a deaf ear the dendrites have often disappeared and one can still stimulate the neuron and or axon. So in deaf subjects it is assumed that the primary stimulation is of the neurons in the spiral ganglion; particularly with the perimodiolar electrodes.

When electrodes are widely spread along the array each electrode has to activate a relatively large proportion of the auditory neurons, in order to be able to affect all neurons available in the spiral ganglion and to do so they require a higher current level than when electrodes are closely spaced and an electrode only has to affect a relatively small proportion of the auditory neurons in order to allow activation of the whole spiral ganglion and thus a lower current level can be used but more stimuli will be needed to activate all auditory neurons. This description is a simplified version of the actual physiological reality but serves to illustrate the principle.

Figure 6A:
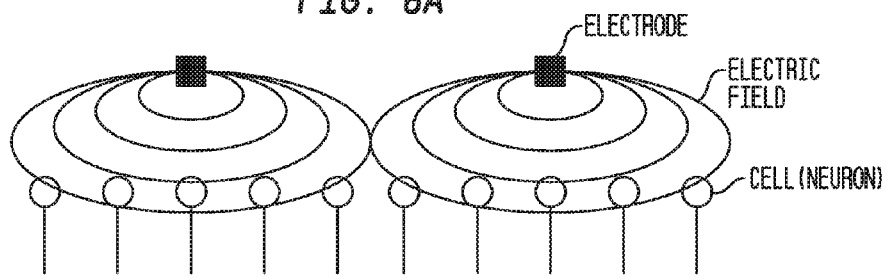
Figure 6B:
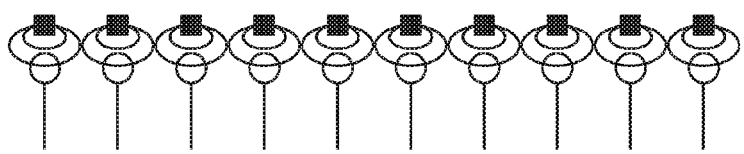

FIGS. 6a and 6b depict electrodes, cells and electrical fields. In FIG. 6a there are only two electrodes and multiple neurons while FIG. 6b shows as many electrodes as neurons. When there are more electrodes there is need for less current but this also means there is a need for more current pulses to be delivered to the electrodes to activate all the neurons. The strategy disclosed herein is intended to enhance resolution of the spectral transmission through arrays with multiple electrodes designed for local control of the activity of the auditory neurons close to the electrodes, through focussed stimulation modes.

One assumption of the strategy is that the spread of excitation within the cochlea will stay relatively constant with increasing pulse rates particularly at the proposed relatively low rates below 1000 pps.

By focussing and localising the excitation fields through near threshold stimulation there is less electrical field overlap and thus less interaction of current fields to each electrode and this will then allow for the implementation of a coding scheme where two electrodes even those located adjacent or close to each other can be activated simultaneously while preserving not only the tone but also the loudness characteristic desired to be perceived by the recipient. Yet further two electrodes, having unused electrodes between them, can be excited and there will be even less likelihood that the electrical fields will interfere with each other. Simultaneous stimulation can be used for creation of virtual pitch channels by balancing the current levels applied on two adjacent or nearby (up to 4 mm apart) electrodes.

Simultaneous and sequential stimulation of adjacent or nearby electrodes can be used to create virtual channels through balancing of the stimulation currents and thus create intermediate pitches between the original pitches evoked by the two individual electrodes, and although this is known, the exemplary embodiment disclosed herein can make use of this approach by appropriate temporal spacing of the virtual channels to avoid field interaction.

To minimize interaction, (recognising that the bands of received frequencies that are being represented by each electrode can be referred to as channels) stimulus sequences are applied using maximal distance between stimuli in place and in time. The optimum coding can be determined each time the received audio signal is analysed (it is typical to use Fast Fourier Transforms (FFT) but it also possible to use combined filters to obtain the power of the pitch and pitch phase information (e.g. vector sum) of the frequency bands) to determine peaks as described previously within selected predetermined bands.

The efficacy of the electrical field decreases by a factor proportional the square of the radius from the source. Note that the electrical field interaction is not by definition the same as the excitation field interaction.

Figure 7:
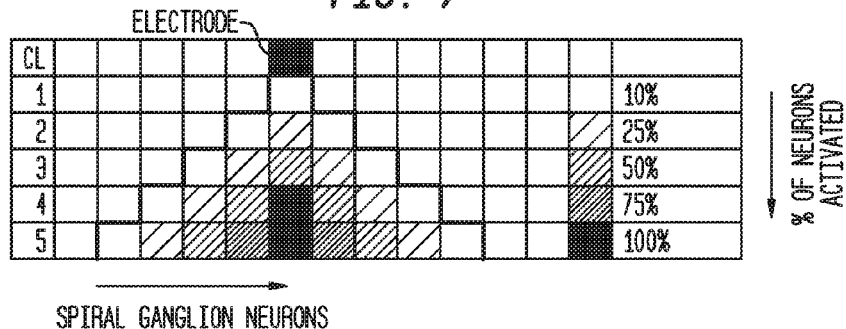

This is depicted pictorially FIG. 7. If the current level (CL) increases the excitation field increases. The percentages are an indication of % of neurons activated. One can see that it is difficult to activate all the neurons in the vicinity of the electrode (e.g. CL5) without also activating proportions of neurons nearby.

The coding strategy proposed in this and other embodiments of the invention takes this spreading phenomenon into account by making use of one or more excitation spreading functions to modify the spectral weighting of the signal to be applied when trying to mimic the received audio signal in the recipient but this excitation spreading function must be based on the available excitable neurons in the vicinity of the specific electrode to be stimulated as well as the capacity of the neurons to be excited by an applied current.

As described above, the spectral power of the frequency bands allocated to the electrodes in the array are obtained through FFT (or other means).

Figure 8:
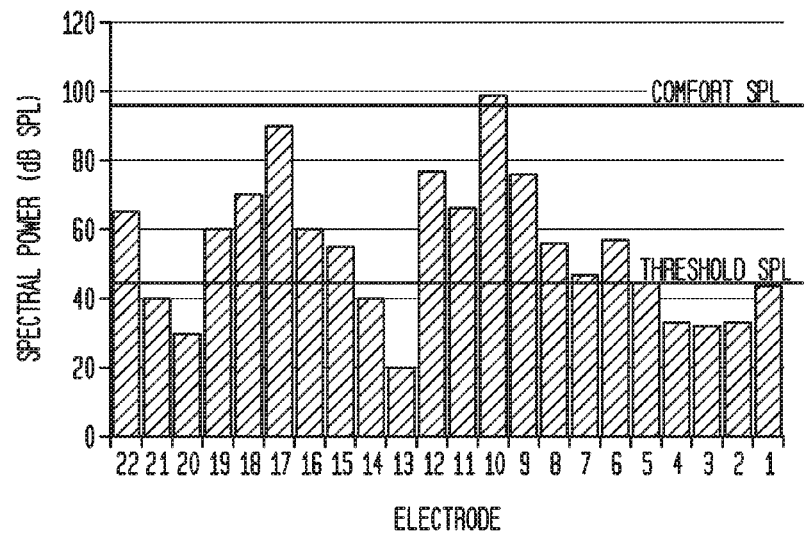
FIG. 8 depicts an example of a Fast Fourier Transform (FFT) according to 22 filter bands allocated to the electrodes; indicating the input dynamic range between Threshold SPL (Sound Pressure Level) and Comfort SP.

One embodiment of the coding strategy described herein, uses the maximum sound pressure values above a predetermined threshold. These levels (in one example the Threshold Sound Pressure Level (TSPL)) are determined from first an analysis of the frequency spectrum of the received signal and once the frequency bands associated with each of the number of implanted electrodes are determined the level of stimulation to apply to the corresponding electrode can be determined (e.g. electrode 10 in the schematic FFT depicted in FIG. 8 depicts that the level is above the Comfort Sound Pressure Level while 12 others are within the range). The use of the TSPL as the level from which to apply either or both the compression of rate and current level dynamic range coding are in fact one strategy that is usable while it is possible without compression of levels above CSPL.

In one embodiment of the coding strategy there is a weighting step included before selecting the next maximum, the spectral powers are weighted based on the excitability of the excitable neurons in the vicinity of each electrode based on a prior mapping using the weighting techniques described in this specification.

Figure 9:
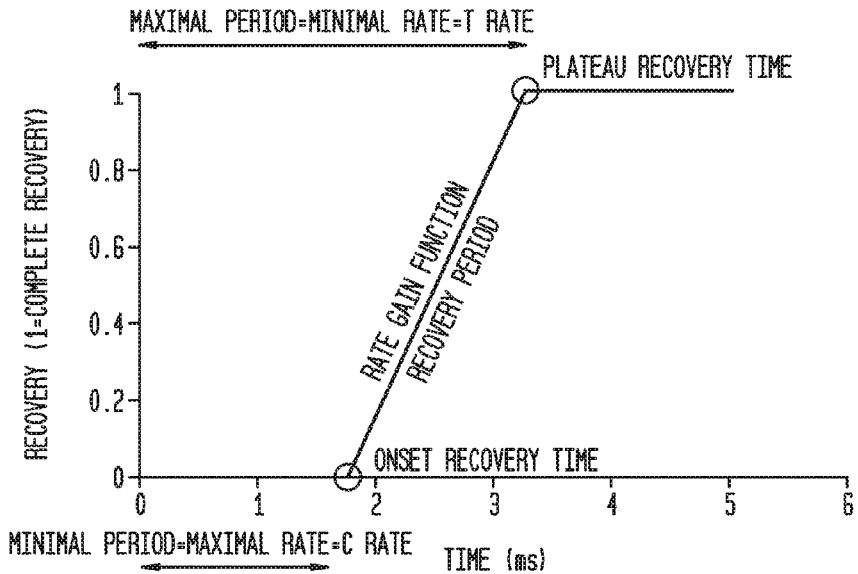
FIG. 9 depicts a schematic of a recovery function.

In this case the auditory neuron recovery function is used to calculate the local excitability at the time of the next stimulus. The recovery function of an auditory neuron is depicted pictorially in FIG. 9 as a function of time, as shown on the x-axis, after activation of a neuron; while the y-axis indicates the probability that a neuron will fire to the next near threshold stimulus after activation. This can be a generic model applicable to any available excitable neuron, thus although a recovery function is a known phenomenon for neurons and excitable tissue, the recovery function can change with the applied current level and that the strategy used by example herein, can be expanded by applying different recovery functions for different current levels and then even use different recovery functions for particular excitation field spreading over multiple electrodes. The y-axis depicts a representation of recovery with values between zero and 1 where 1 represents complete recovery; the x-axis shows time in milliseconds ranging from zero to 6. The period zero to just less than 2 milliseconds is referred to as the minimal period representative of the maximal rate the C rate and relates to the onset recovery time. Then the recovery period commences and exhibits a rate gain function as the recovery values change from zero to the value 1. The period between onset recovery time and plateau recovery time controls the dynamic range of rates that can be applied to be effective. When complete recovery is reached, that is the value is 1, time from zero time is the plateau recovery time period which thus indicates that recovery is maximally complete. The period of time from zero to complete recovery is shown in FIG. 9 as about 3.25 milliseconds and is the maximal period, and this indicates the minimal rate or T rate which is the longest inter pulse interval that will be useful.

One way in which the proportions of excitable neurons are calculated uses a physiological excitability model based on refractoriness, spread of excitation and adaptation. The weighting factors are calculated for each electrode in the stimulation array.

The recovery function provides a corollary indication of the excitability of the auditory neurons. In the strategy described in this embodiment the variable excitability of auditory neurons in the vicinity of an electrode is used to weight spectral powers and thereby control stimulation by changing the stimulation pulse rate to mimic sound level pressure (loudness).

It is useful to determine what elements constitute an Excitability Model and it is considered that the following are useful indicators for determining the receptiveness at any time of a neuron to stimulation delivered as a current from an implanted electrode in the cochlea of a recipient:

"Recovery Functions"
"Spread of Excitation Functions"
"Adaptation"

Recovery Functions

Recovery Functions can be defined by:
1. An 'Onset Recovery Time' controlling the fastest stimulation rate C by setting the shortest possible inter pulse interval. Physiologically this represents the absolute refractory period during which neurons are not excitable.
2. A 'Plateau Recovery Time' controlling the slowest stimulation rate by setting the longest inter pulse interval the T rate. Physiologically this represents the onset of the plateau at which neurons complete recovery from stimulation and are fully excitable.
3. The 'Recovery Period' between onset recovery time and plateau recovery time controls the dynamic range of rates. Physiologically this represents the relative refractory period during which neurons are recovering from the previous stimulation and slowly become fully excitable.
   a. The recovery period controls the rate gain through the weighting of the spectral power. The rate gain function can have different curvatures and shapes.
4. A 'Summation Time' representing summation effects of stimulation fields at short inter stimulus intervals (<300-500 microseconds). Summation effects increase exponentially when intervals become shorter.
5. A "Super-excitability" phase with an optimum close to the Plateau recovery Time.
6. The Recovery Functions can be based on electrophysiological and psychophysically measured functions of the implant subject or a subject group.
   a. Recovery Functions measured electrophysiologically include those recorded through measuring electrically Evoked Compound Action Potentials (ECAPs) using Neural Response Telemetry (NRT), those recorded through measuring of Electrically Evoked Auditory Brainstem Response (EABR) and those recorded through measuring of Cortical Evoked Responses using either an external system or the cochlear implant (CI) system for recording of these potentials. Potentials recorded through the CI can be stored in an internal memory and can be transmitted to the external equipment.
7. In the Physiological model used in a coding strategy the Recovery Functions use for convenience values between 0 to a plateau of 1 but other values can be used to designate the boundary values. In this embodiment, the value of 1 implies that the respective neurons are fully excitable by a stimulus field.
   a. The implementation may also contain values above a maximum in this embodiment above 1. E.g. for the implementation of super-excitability.
   b. Super-excitability can also be implemented by lowering the plateau value below 1. The Super-excitability peak can still be kept below 1.

Spread of Excitation

A Spread of Excitation Function (SOE) defines the spatial distribution of excited neurons along the spiral ganglion as a result of the application of an electrical stimulus to one or more electrodes implanted in the cochlea.
1. This Spread of Excitation Function is used to calculate excitability based on proportional activation of neurons allocated to electrodes in the vicinity of the stimulating electrode(s) and depends on the level of the stimulus/stimuli previously applied.
2. When stimulation levels increase:
   a. The local excitation levels increase; and
   b. excitation spreads towards neurons allocated to neighbouring electrodes.
3. The Spread of Excitation functions are defined as function of electrode array and can be described by:
   a. A peak value which is at or close to the stimulation electrode
      i. The peak can be narrow and be allocated to neurons of only one electrode
      ii. The peak can be broad and spread over a neurons allocated to a range of electrodes
   b. An apical spread function defined by a slope and/or shape as a function of electrode distance from the stimulation site
   c. A basal spread function defined by a slope and/or shape as a function of electrode distance from the stimulation site
4. The Spread of Excitation functions can be based on electrophysiological and psychophysically measured functions of the implant subject or a group of implant subjects.
   a. Spread of Excitation functions measured electrophysiologically include those recorded through measuring Electrically evoked Compound Action Potentials (ECAPs) using Telemetry from implant to external device (NRT).
   b. They can be measured using simultaneous and forward masking paradigms.
5. In the Physiological Excitability Model used in the coding strategy of at least one embodiment the Spread of Excitation function contains values representing evoked activity along the spiral ganglion and they run from 0 (no neurons excited) to 1 (all neurons excited). The value of 0 implicates that no neurons are excited and a value of 1 implicates that all neurons are excited.
6. The Spread of Excitation functions along the electrode array can be a function of stimulation rate and/or available excitable neurons so as to accommodate the existence of dead or partly dead regions. The Spread of Excitation functions may decrease or increase in width during successive stimulation and they may adapt during successive stimulation for prolonged periods.
   a. The values of the slopes of the Spread of Excitation functions indicate the proportion of auditory neurons activated in the (Physiological) Excitability Model used in the disclosed coding strategy.
7. The Spread of Excitation functions are recipient specific and are defined for all stimulus Current Levels and Electrodes used and/or "virtual" channels as will described below and in greater detail later in the specification.
8. The peak of the Spread of Excitation functions can have an offset with respect to the stimulation electrode and the Spread of Excitation functions may contain multiple peaks.9.

The SOE function can be calculated at a higher resolution than the number of electrodes. The resolution can be based on the number of virtual channels (e.g. 2 adjacent or nearby electrodes activated simultaneously or in close succession) or on the auditory neurons available in the spiral ganglion.

Adaptation

Adaptation is defined as the decrease of neural response over time to a sustained stimulus.

Adaptation effects are relatively long term effects (seconds-minutes-hours) and increase when auditory neurons are stimulated at a high stimulation rate almost regardless the current level. Recovery from Adaptation takes place over seconds-minutes and starts when neurons are no longer stimulated or stimulated at low rates (<±100 pps) that appear to not induce Adaptation.

However, it should also be noted that the inventor identifies that the current level has some effect. Close to the stimulation electrode the electrical current field is at its largest and neurons are more easily firing in response to supra threshold stimuli. The neurons that are activated through far field stimulation will have a lower firing probability and therefore the SOE function will adapt most likely towards more focussed stimulation during sustained high rate stimulation. E.g. the activation of neurons allocated to nearby electrodes decreases proportionally to the proportion of the neurons available for activation. For instance if all neurons are excitable, 50% can be activated and when 50% of the neurons are available a proportion less than 50% is activated. The decrease in the proportion that can be activated depends on the available proportion, and decreases with the distance from of the stimulating electrode.

The aim is to minimize long term Adaptation effects by slowing of the stimulation rate when adaptation occurs and particularly when it occurs at the stimulation site.

Adaptation is implemented 'by modifying the "Recovery Functions" based on historical stimulation rates. During high rate stimulation, the Recovery Functions adapt to lower the stimulation rate. During no stimulation or low rate stimulation the 'Recovery Functions" are adapting in the opposite direction towards their original shape, mimicking recovery from adaptation, and thereby allowing higher stimulation rates to be applied again.

1. Adaptation of the "Recovery Function" during high rate stimulation can be implemented by:
   a. A slow decrease of the plateau value of the "Recovery Function".
   b. A slow adaptation of the Rate Gain Function including a decrease of slope, lengthening of the 'Onset Recovery Time' and lengthening of the 'Plateau Recovery Time'.
2. Recovery from modification of the "Recovery Function" during low rates and no stimulation can be implemented by:
   a. A slow increase of the plateau value of the "Recovery Function" towards the original value.
   b. Adaptation of the Rate Gain Function towards the original values.
3. Adaptation time constants can be based on subject preference and electrophysiological measures using Electrically evoked Compound Action Potentials (ECAPs), EABR, CER recorded through external devices and/or implant and transmitted through telemetry As shown in FIG. 9 until the onset recovery time is reached an activated auditory neuron is in the absolute refractory period and cannot be further stimulated. Thus a recovery function value of zero implies that none of the activated auditory neurons are available for stimulation and by applying a weighting of zero to the respective spectral peak, the applied stimulation will be controlled to zero. If the spectral peak is only allocated to 1 electrode and stays in the same band for some time, the next stimulus can occur the earliest moment that auditory neurons again become available for stimulation which is at the beginning of the recovery period. Thus it may be excluded from being stimulated during the next cycle of stimulation, even though the sound pressure level has been determined to specify that the respective electrode is to be stimulated.

The first time that an auditory neuron can be stimulated again (or shortly after) is directly dependent on the onset recovery time and therefore one can say that 1/(onset recovery time in seconds)=the maximal applicable rate in pulses per second for updating the stimulus of an electrode i.e. the cycles for update are variable dependent on the recovery time. Put another way the recovery function indicates the probability that a neuron will fire to a stimulus; so if the cycles are stimulation cycles one can say that the shortest cycle (and thus the highest rate) at which a stimulus can become effective again equals to the onset recovery time.

Figure 10:
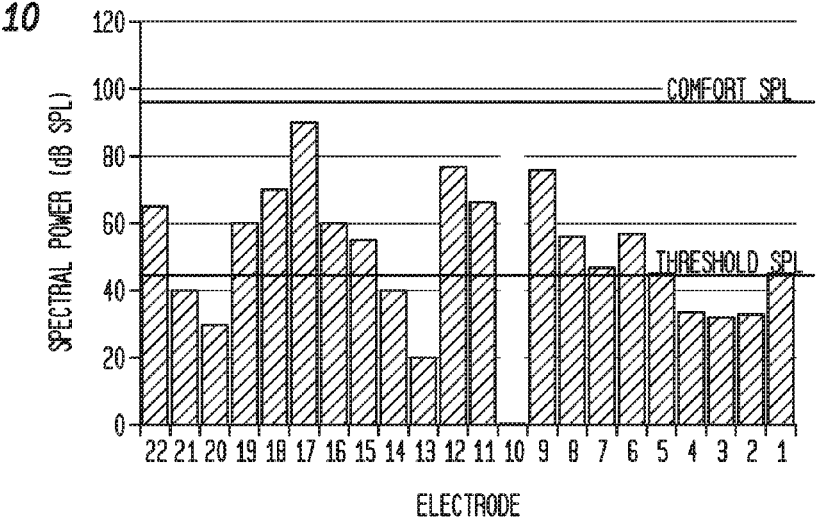
FIG. 10 depicts the results of an FFT process over a received audio signal depicting various bands associated with a respective electrode after stimulation of an electrode.

FIG. 10 depicts the results of an FFT process over a received audio signal depicting various bands associated with respective electrodes after stimulation on electrode 10 (which was the largest peak in the FFT as seen in FIG. 8. In this case the weighting of the spectrum has been applied to the whole power (in SPL) allocated to the electrode and directly after stimulation it is set to 0 as the recovery function is still within the absolute refractory period with a weighting of 0.

The weighting can be applied to the absolute power (SPL) of the spectral peak. Directly after a stimulus the recovery function starts with a weighting of 0 and then runs at 0 until the onset recovery time has passed (=absolute refractory period after activation/stimulation). Stimulation can only occur when the spectral power level is above threshold. Therefore a weighting value above (Threshold SPL/Spectral peak SPL) is needed to get back to a spectral power above TSPL and the fastest rate would occur at CSPL with a stimulus period that can be deduced from the recovery function using a weighting factor (=proportion of excitable neurons) of TSPL/CSPL. One can also apply the weighting only to the Dynamic Range (=CSPL−TSPL) and the shortest time for the next stimulus to become effective (i.e. a weighting above 0) would be just after the onset recovery time.

Application of weighting to the Dynamic Range causes channels with spectral peaks above threshold to be stimulated at the fastest rates; particularly when the total stimulation rate allows stimulation of all electrodes within the absolute refractory period, and particularly at the beginning of a stimulation or after a period of silence during which all neurons have completely recovered to a weighting of 1.

During high rate stimulation relatively small proportions of neurons are activated as most neurons will be recovering from previous activations. It depends on the time between the absolute recovery time and the plateau recovery time and the slope of the recovery period how much spread there is in stimulation rates at the available channels.

Figure 12:
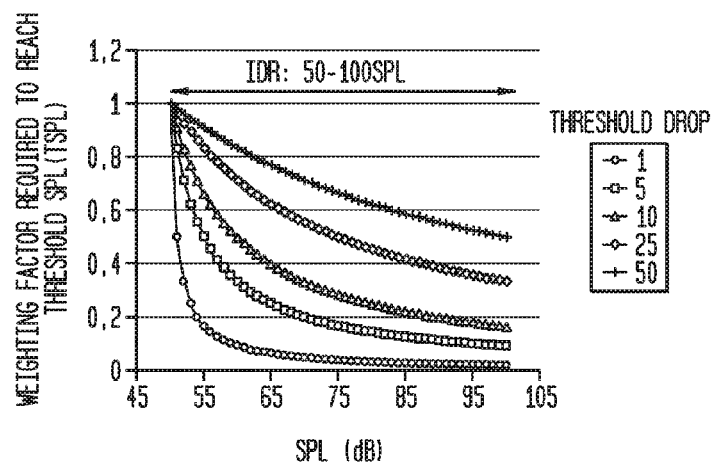
FIG. 12 depicts a graphical representation of the effect of different weighting factors for the Sound Pressure Levels (SPLs) within the Input Dynamic Range (IDR) that are necessary to reach Threshold SPL (TSPL.

The distribution of rate is related to the weighting factors needed to reach threshold. The weighting factors to reach threshold depend on the range to which the weighting is applied and on the SPL level set at a weighting of 0. The SPL level set at a weighting of 0 can be seen as a Threshold Drop with respect to the Threshold SPL of the Dynamic range. FIG. 12 shows a range of curves depicting the weightings necessary for reaching Threshold SPL for different Threshold Drops when weighting is applied to the (Dynamic range+Threshold Drop z−CSPL−TSPL+Threshold Drop).

In FIG. 12, it can be seen that with a small Threshold Drop of 1 only small weighting factors are needed to reach threshold over a large range of higher SPLs, while only a small range of lower SPLs is available over which rate is truly dynamic. Applying the weighting to the dynamic range is not an ideal implementation. On the other hand the maximum stimulation rate is restricted to a stimulus period (deduced from the recovery function) corresponding to a weighting of TSPL/CSPL, if the weighting is applied to the whole power (e.g. FIG. 12; threshold drop of 50 and the alternatives disclosed are described in greater detail later in the specification). This disclosure includes range of fixed proportions lower than the TSPL up to TSPL to adapt for the stimulation rate ranges available to the coding strategy. The disclosure also includes dynamic changes in Threshold Drop, Recovery Function and Spread Of Excitation Function based on the power in the spectrum and historical stimulation.

In this example a TSPL of 50 dB and a CSPL of 100 dB is used, the vertical axis represents the power in SPL of the spectral band, the vertical axis represents the weighting factor needed for a for a certain power (SPL) to reach TSPL. The curves represent the weightings factors needed to reach TSPL for different "threshold drops" values. Weighting is applied to [SPL−TSPL+threshold drop]. The weighted SPL are calculated by: [TSPL−threshold drop+weighting factor×(SPL−TSPL+threshold drop)]. The weighted SPL reaches TSPL when the weighting factor=threshold drop/(SPL−TSPL+threshold drop).

Figure 14:
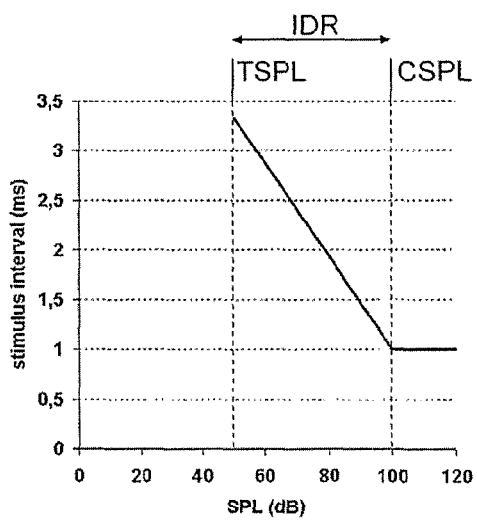
FIG. 14 depicts a function of stimulus interval to sound pressure level (SPL in dB) to illustrate a simple alternative to rate coding without the use of an excitability model.

FIG. 14 depicts a function of stimulus interval to sound pressure level to illustrate a simple alternative to rate coding without the use of an excitability model. In this figure the stimulation intervals (=1/stimulation rate; in seconds) are given for different SPLs of the FFT. Another alternative implementation could make use of the overall power of the spectrum. In this implementation the overall power of the spectrum is used to set the maximal total stimulation rate and then redistribute the rates over the channels. It should be clear that this disclosure includes simple implementations of rate coding that do not make use of an excitability model. It is clear that one could develop a strategy in which stimuli are based on the stimulus interval (=1/rate) allocated to the SPLs within the input dynamic range to achieve a usable rate coding of loudness. The problems that one has to resolve for such implementation relate to the planning of actual and future stimuli based on historical stimulation.

The disclosure includes the possibility to adopt the total stimulation rate to the available total power in the spectrum to get a balanced distribution of rates in line with the spectral power. E.g. the higher the power of the sum total of the spectral bands the higher the total stimulation rate.

Experimentation with simulations will show how to best arrange the relation between the recovery function weightings, the fixed proportion below the stimulation rate and the total stimulation rate.

As depicted in this example in FIG. 9, after about 1.8 ms the excitability in the vicinity of the respective electrode begins to recover and it will take about 3.2 ms before the auditory neurons are fully recovered and the peak is again weighted at a maximum proportion of 1 or any other applicable excitability function determination.

Figure 11:
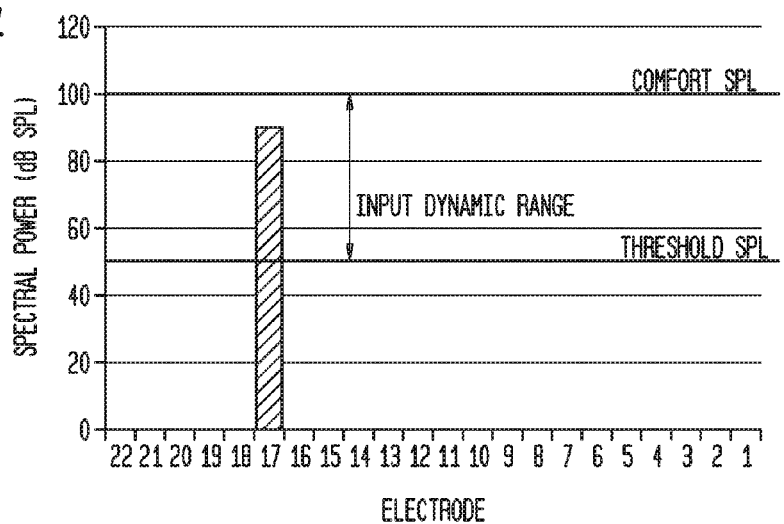
FIG. 11 depicts the dynamic range of the spectral power as determined by the comfort and threshold sound pressure levels.

As depicted in FIG. 11 the Dynamic Rate Range (DRR)= highest rate−lowest rate for a given electrode ideally covers the whole Input Dynamic Range (IDR) which lies between T (threshold) SPL and C (comfort) SPL. Sounds above C-SPL can be compressed to C-SPL.

In the ideal case: T (threshold) SPL generates the lowest rate=1/(plateau recovery time) and the C (comfort) SPL generates the highest rate=1/(onset recovery time).

After a stimulus has been applied to a given electrode the spectral power level of that electrode will be reset by the weighting factor (based on the excitability given the recovery function). The first period in the recovery function (the absolute recovery time) is a time period during which the excited auditory neurons are not excitable and the applicable weighting factor for these neurons is zero.

During the recovery period the recovery function factor value, used for the weighting, is increasing. A received sound pressure level at the Threshold (TSPL) requires a weighting factor of 1 (plateau recovery time) to at least return to threshold and the electrode will be selected for stimulation again and thereby stimulating this channel at the lowest possible rate.

The principle is that the TSPL translates to the lowest rate while the CSPL translates to the highest rate. If current level is includes the TSPL will translate to the lowest rate and the lowest CL and the CSPL translates to the highest CL and the highest rate. Intermediate SPLs translate to intermediate CLs and intermediate rates.

A power level at comfort level (CSPL) should use a just above 0 weighting factor to come back to threshold wherein only spectral peaks above threshold are stimulated to assure a rate corresponding to 1/(onset recovery time). If weightings are applied to the absolute SPLs, a CSPL will reach threshold at a weighting of TSPL/CSPL. e.g. if CSPL=100 and TSPL=50; CSPL will reach threshold after stimulation at a weighting of 100/50 (=0.5) which would be half the rate range in the case of a linear recovery function. Note that in accord with earlier description the current levels are allocated to the spectral powers of the original spectrogram. The weighted spectrogram is used to control rate. As indicated above the total stimulation rate is a factor that needs to be taken into account to assure that there will be a distribution of rate.

To assure that CSPL reaches TSPL shortly after the onset recovery time the spectral power can be fixed just below TSPL (e.g. a reduction factor of 1 dB would set powers fixed at TSPL-1 db) and the weighting is only applied to the Input Dynamic Range (IDC)+reduction factor.

Figure 13:
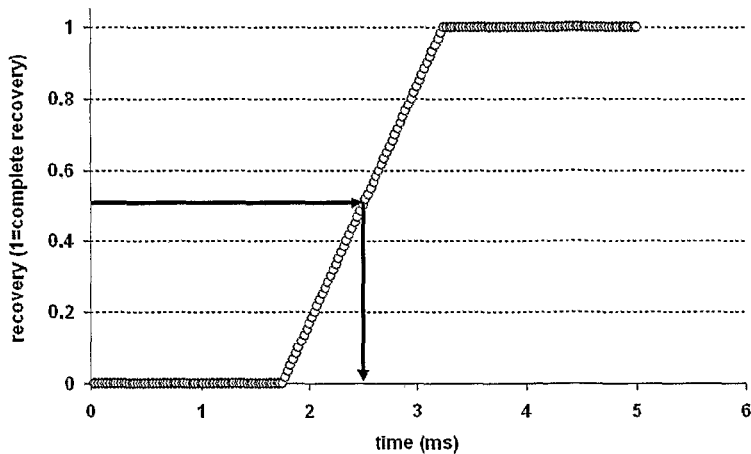
FIG. 13 depicts graphically a recovery function and shows how a weighting factor can be directly translated into a stimulation period which can then be translated to stimulation rate.

FIG. 12 shows the effect of applying various weighting factors for the SPLs within the Input Dynamic Range that are necessary to reach TSPL. In this figure you see the weighting factors used to reach TSPL for different threshold drops. One can see that with increasing threshold drop the whole range of applicable weighting factors decreases while the dynamic region of applicable weighting factors increases. Weighting factors can be directly translated into stimulation rate. E.g. a weighting factor of 0.5 would use a recovery up to 0.5, which translates to a period of 2.5 ms, which translates to a rate of 400 pulses per second (as depicted in FIG. 13).

The range of weighting factors translates to a range of periods on the recovery function, which translate to a range of pulse rates. The range of weighting factors to reach threshold controls the rate at different SPLs and becomes less linear with a decreasing reduction factor and most of the rate variability will occur at the lower SPLs. Ideally the range of rates is maximally used for creation of different loudness precepts which can best be reached by a linear function of weighting factors.

In some patients loudness coding by rate will not create enough loudness and then rate can be used at the lower SPLs while current levels increases are distributed over the higher rates. In these cases one might consider to be better off with a less linear function including by introduction of only a small reduction factor of TSPL. Rate is used for coding of loudness at the lower SPLs while CL is used for coding of loudness at the higher SPLs. A range of CLs distributed over the whole range or part of the upper range of available SPLs can be included in subjects that do not experience enough loudness based on rate only. This is particularly useful for subjects that make use of cochlear implant electrode arrays with less than 20 electrodes.

The most effective implementation of the weighting factor in combination with the recovery function and the total stimulation rate is a matter of experimentation as will be apparent from the various examples provided and further described later in this specification for various recovery functions.

It is known that cochlear implant recipients suffer a compromised dynamic range (i.e. they have less distinguishable loudness steps compared to a normal hearing person). Thus one of the preferable outcomes is to arrange the coding so that the rate range available is optimally used for coding of loudness and includes at least the most relevant rate steps, e.g. if loudness increases linearly with rate and rate steps of 1 pulse per second (pps) are distinguishable, the coding should be arranged so that they are implemented within the relevant dynamic range to the recipient.

A simple alternative to rate coding could be to allocate a stimulus interval in ms to a SPL which is but one of many alternatives. This approach relates to one channel and the associated rate coding and does not take into account temporal effects which are accounted for in the excitability model.

The disclosed strategy makes use of the recovery function and weighting of the spectrum to code rate. The alternative suggested here, is a simple version, where rate is not dependent on the local excitability but just hardcoded against SPL. This coding can be further specified, e.g. loudness is not only an instantaneous phenomenon but also includes a time integrator, and an advanced version could include a running average of the spectral bands to calculate the loudness and set the rates. Furthermore, it should be noted that 4 ms are needed for a pulse train of 2 pulses at a rate of 250 pps while 1 milliseconds is needed for two pulses at 1000 pps. The time window of the integrator could e.g. be 5 ms with an update rate of 1000 sec−1.

Figure 15:
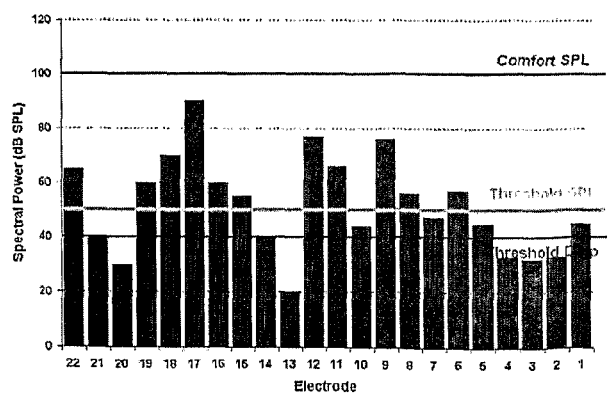
FIG. 15 depicts an example FFT analysis of a received audio showing a bar graph with Spectral Power (dB SPL) on the y-axis for each of the bands selected for each of the electrodes EL1 to EL22 showing Comfort SPL, Threshold SPLs as well as a Threshold Reduction SPL (Threshold Drop)

When a "Threshold Reduction Factor" is included in considerations as to what stimulus to apply to electrodes in the array, the FFT determined from the received audio input depicted in FIG. 15 can be analysed as a starting point. There are 11 peaks above Threshold SPL in FIG. 15 and if there was no stimulation of an electrode before, the weighting would be 1 for all electrodes and all peaks shown above the threshold level can be picked for stimulation. The applied current levels can be threshold when only rate is used for loudness coding and they can be a range of current levels allocated to the SPLs within the dynamic range. All peaks above threshold will be picked for stimulation but only if the total stimulation rate is high enough to pick all peaks within the absolute refractory period.

Peaks are picked and the total stimulation rate used determines how much time it takes to stimulate all above threshold peaks.

For example, there can be a total possible/available stimulation rate of 20 kpps. This implies that the 11 peaks can be stimulated within an 11*0.05=0.55 ms period. If this period is within the absolute refractory period of the recovery function all peaks will still be weighted with a value of 0 and be below Threshold SPL.

Figure 16:
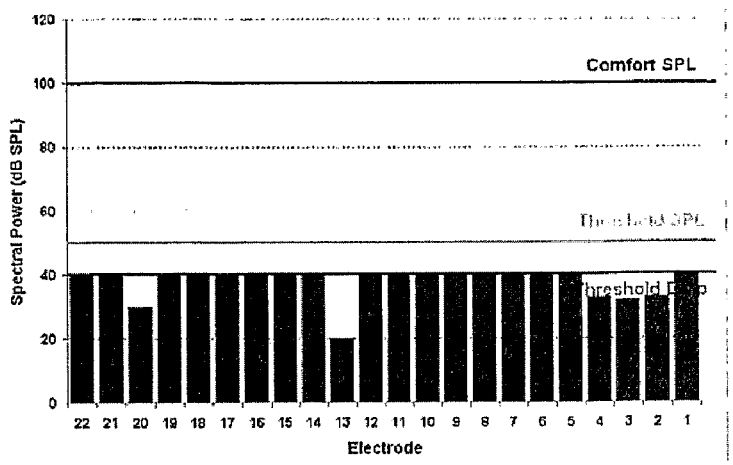
FIG. 16 depicts an example FFT analysis of a received audio showing a bar graph with Spectral Power (dB SPL) on the y-axis for each of the bands selected for each of the electrodes EL 1 to EL22 showing Comfort SPL, Threshold SPLs as well as a Threshold Reduction SPL (Threshold Drop) wherein the peaks are adjusted by weighting after stimulation of all channels within the absolute refractory period preceding the onset recovery time indicated in FIG. 9.

If the Threshold Reduction Factor is used (as shown in FIG. 16) there are 17 peaks that reach that level.

In this example we have an FFT update rate of 1 kHz: this implies that after stimulation of all peaks the FFT has not been changed.

The weightings are increasing after the recovery onset time and it is clear that the power on EL17 will be the one that was first stimulated and thus also will first be weighted with higher weightings and increases then until Threshold SPL at which time the next stimulus will be allocated to EL17.

This example highlights that in the running coding strategy the peaks will be picked before they have a chance to get well above threshold and the highest peaks will be picked more often (and thus stimulated at a higher rate) as they will more often reach Threshold SPL.

As already disclosed it might be that it will be needed to set the Threshold Current level above the measured threshold current level. One could also use a range of current levels for the higher spectral powers: for example, in the example above from 80-100 dB one could include a range of 5 Current Levels linearly divided over the 20 dB which would be 0.25 Current level/dB. The excitability model would include increasing excitation spread functions with increasing current level to better control the neural activity along the spiral ganglion.

Figure 17:
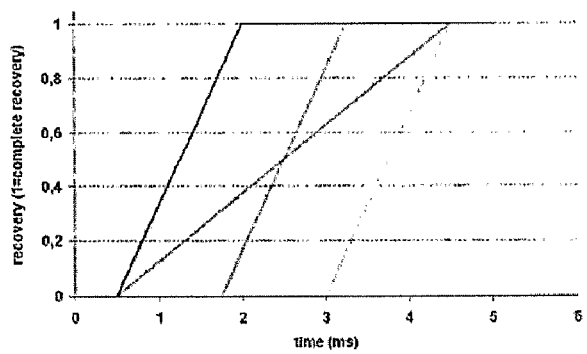
FIG. 17 depicts an example recovery function.
Figure 18:
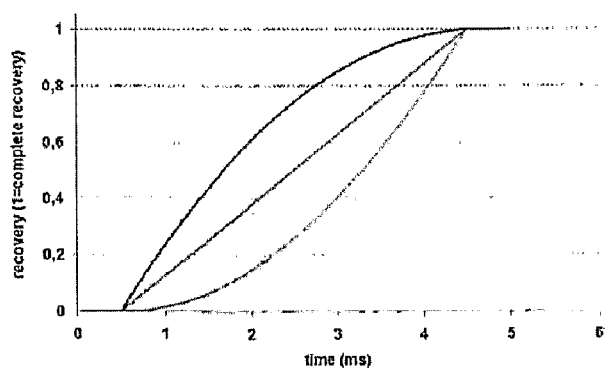
FIG. 18 depicts another example recovery function.
Figure 19:
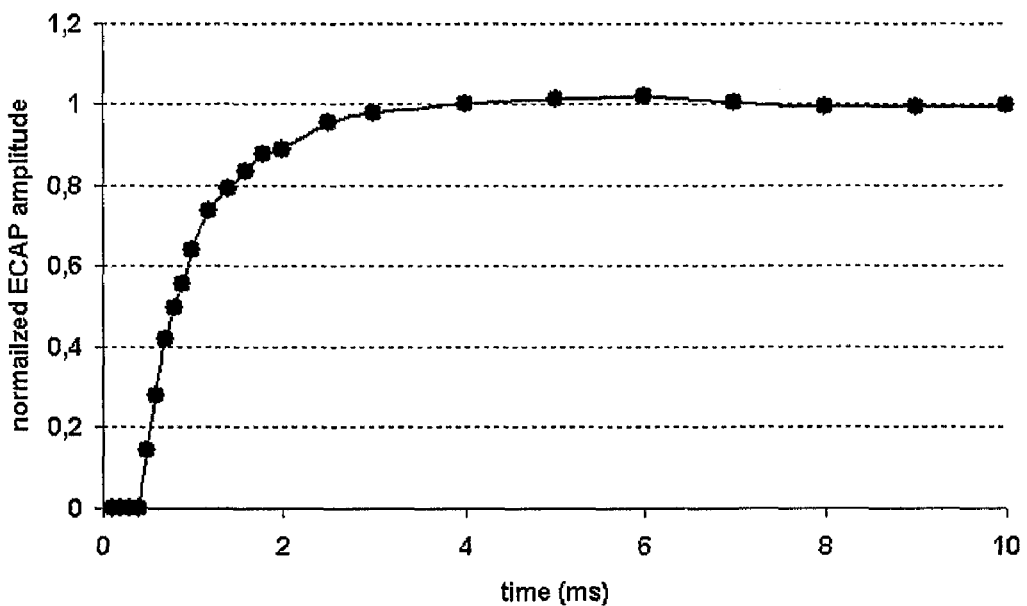
FIG. 19 depicts a graph showing the normalized Electrically Evoked Compound Action potential (ECAP) amplitude against time; The ECAP is normalized against the plateau value at the end of the function.
Figure 20:
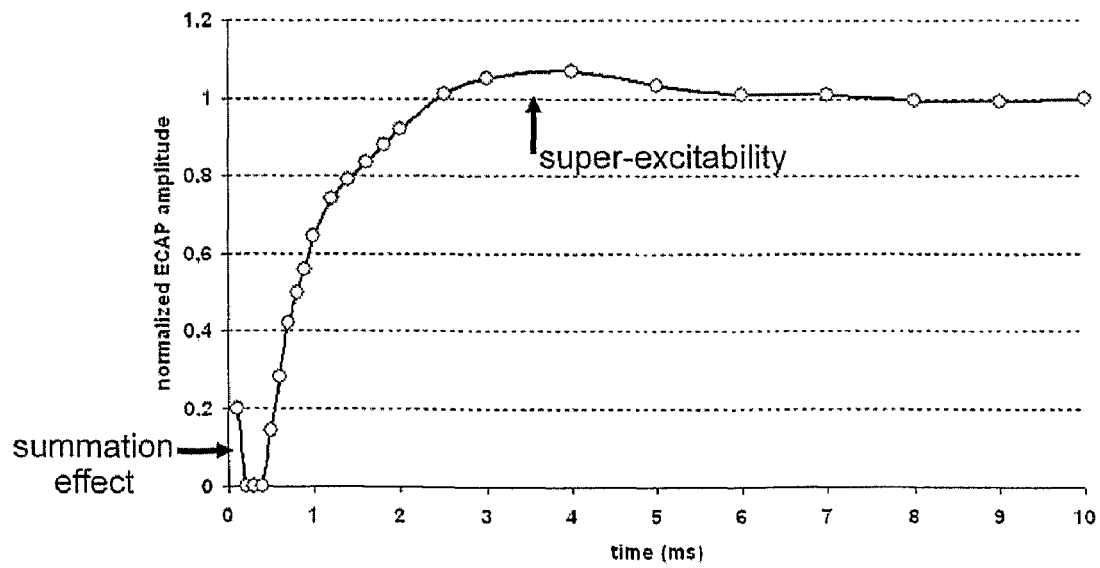
FIG. 20 depicts a graph showing the normalized ECAP amplitude against time including a recovery function with "super-excitability"; The ECAP is normalized against the plateau value at the end of the function.

Examples of recovery functions are given above and it will be understood that different recovery functions could be used, as for example those depicted in FIGS. 17 and 18 or a recovery function can be based on neurophysiological measurement, and include a super-excitability phase (known from NRT measurements) in which the excitable proportion is elevated above the plateau phase during a certain period (FIGS. 19 and 20). This super excitability phase particularly shows up in NRT measurements when the masker current level
is lower than the probe current level. The origin of super excitability is not well understood and experiments will show its relevance for the coding strategy disclosed herein.

After stimulation an electrode can be stimulated again before the plateau phase has been reached. This implies that only a proportion of neurons will be ready for stimulation. The excitability model that calculates the excitability takes this into account by letting the previously activated proportions of neurons recover according to the previously started recovery functions using an adapted plateau value reflecting the involved proportions.

Figure 21:
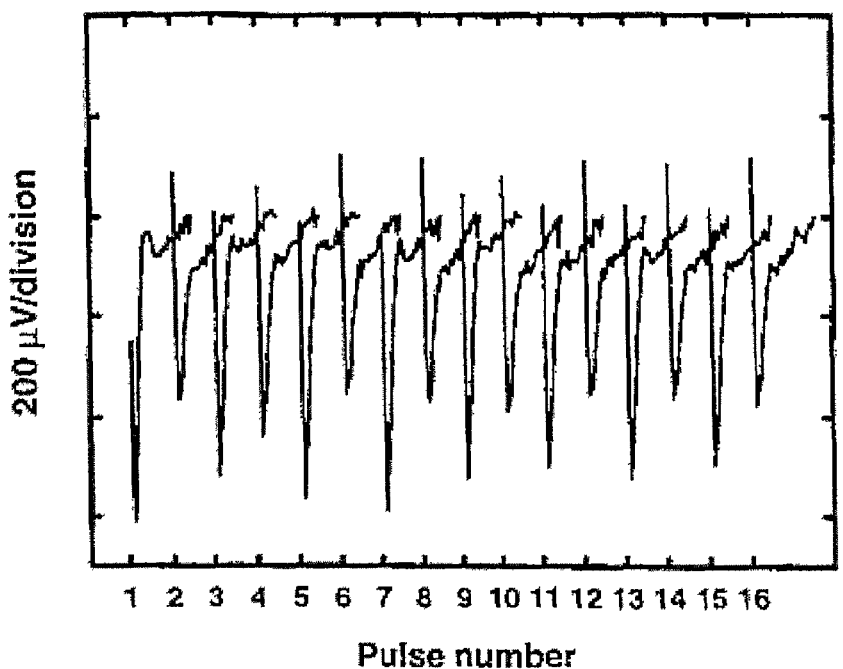
FIG. 21 depicts ECAP waveforms of the auditory neurons when stimulated with a series of pluses with fixed amplitude at a rate of 1000 pulses per second.

This model can explain the oscillating behaviours seen in neurophysiological ECAP measurements during stimulation with pulse trains as depicted in FIG. 21 which is a text book graph of a series of waveforms showing response to a series of pulses with fixed amplitude presented at a rate of 1,000 pulses per second. Response to each successive pulse in train is shown as a function of pulse number. Responses show alternation in amplitude of response that is typical of these data.

Figure 22:
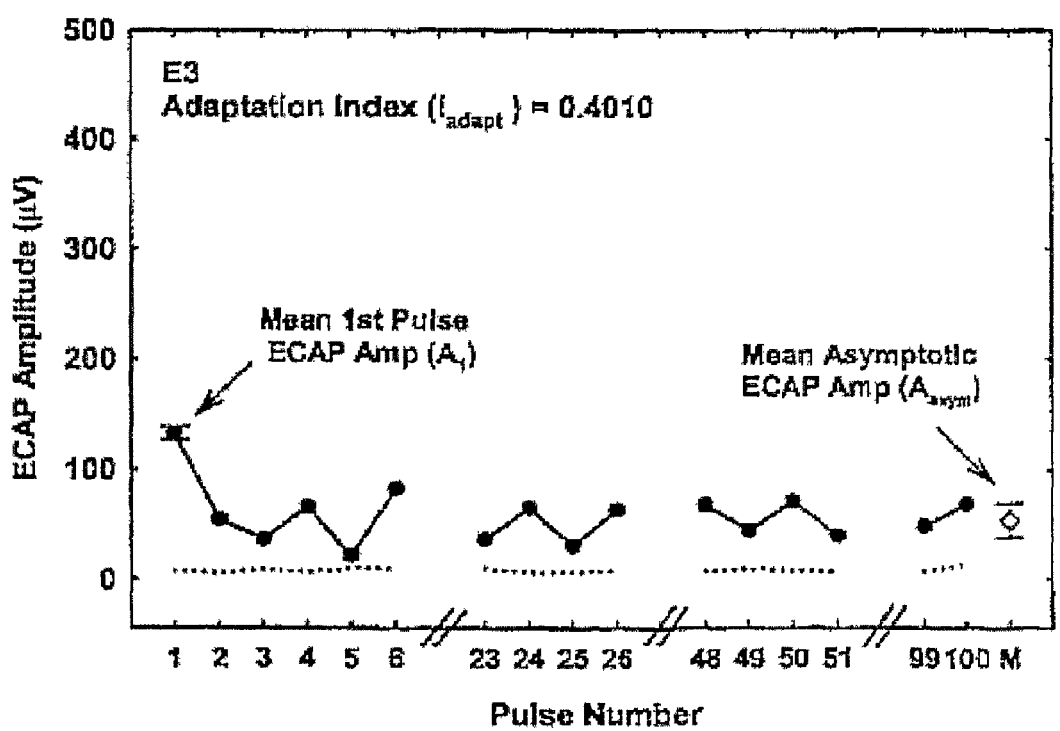
FIG. 22 depicts the ECAP amplitude of the auditory neurons when stimulated with a series of pluses with fixed amplitude at a rate of 1000 pulses per second.

FIG. 22 depicts a textbook ECAP amplitude for one individual electrode as a function of the pulse number in the 1000 pps pulse train. The hash marks on the abscissa indicate that the axis is not continuous. The dotted line represents the amplitude of the noise floor in the recording system. The mean first pulse ECAP amplitude (A1) and the mean asymptotic ECAP amplitude (Aasym) are depicted, the later being shown with a +1-standard deviation bars.

Dead Regions

It is anticipated that some severe or profound hearing impaired persons have dead or partially dead regions along the spiral ganglion. As a consequence some electrodes will have no or reduced amounts of auditory neurons in their vicinity. However thresholds can be obtained with these electrodes as they will activate neurons in the vicinity of adjacent or nearby electrodes through spread of electrical field at higher current levels. Including electrodes above dead regions in the stimulation patterns of the coding strategy can have a negative effect on performance as they put an emphasis on the frequencies allocated to the nearest electrodes with living neurons in their vicinity. These auditory neurons will be stimulated at relatively high rate as they will receive stimuli triggered on a broad frequency band of the sound spectrum. Electrodes in the vicinity of dead regions are best excluded from stimulation. Several fitting approaches are disclosed for dead and partly dead regions:

1. The frequency bands allocated to dead regions are no longer stimulated and they do not have an effect of the frequency bands of the FFT.
2. The frequency bands allocated to electrodes in the vicinity of dead regions are added to the nearest electrodes with living auditory neurons in their vicinity.
3. The frequency bands allocated to dead regions are redistributed over the electrodes that have living neurons in their vicinity
   a. The redistribution can be compressed in such a way that there still is maximal resolution in the frequency bands for speech.
   b. The redistribution can be compressed in such a way that there still is maximal resolution in the frequency bands for music.
4. The dynamic rate range of electrodes allocated to partly deaf regions can be compressed to higher rates to assure their audibility.
5. The Spread of Excitation functions used in the excitability model of the disclosed coding strategy can be accommodated to reflect the actual regions that are activated in the spiral ganglion.

Methods to Identify Dead and Partly Dead Regions:

1. Through Electrically Evoked Compound Action Potentials (ECAP) of the Auditory Nerve:

Spread Of Excitation (SOE) measurements through ECAPs measured with Neural Response Telemetry can be used to probe for dead regions.

Pictorial illustrations are provided in FIGS. 25 to 28 showing the technique for identification of dead regions using Spread Of Excitation measurements through ECAP measurements (SOE/ECAP).

Figure 25:
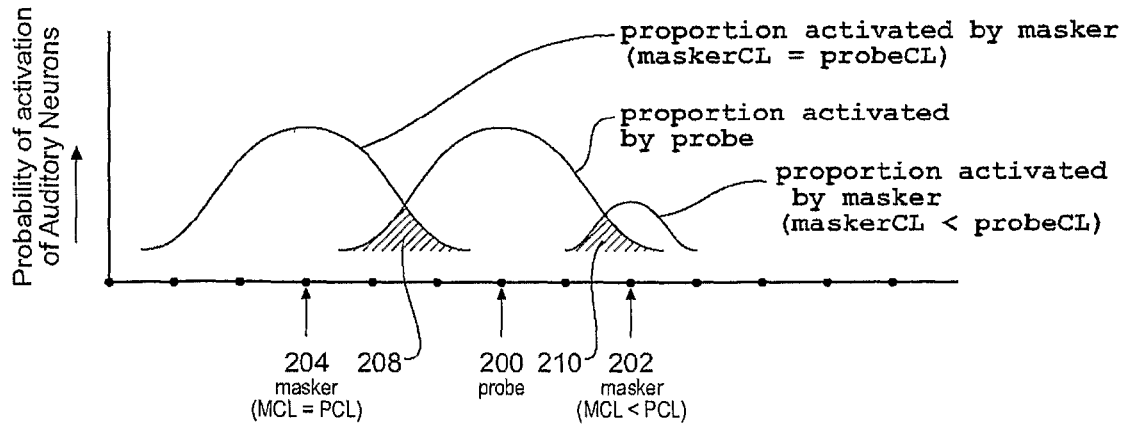
FIG. 25 shows the principle of a Spread Of Excitation (SOE) measurement obtained through ECAP measurements using a masker and appropriate current levels.

FIG. 25 shows the principle of an SOE/ECAP measurement using a probe and a masker and appropriate current levels. Two stimuli are used: a Probe 200 and a Masker 202 and 204 showing the proportion of neurons activated on the y-axis and electrodes along the x-axis. The probe is fixed to one electrode and the masker is presented on a range of electrodes to obtain ECAPs for these masker electrodes. The ECAP measurement makes use of a forward masking technique and therefore only the neurons that are both excited by the masker and probe are visible in the ECAP measurement (shaded areas 208 and 210). FIG. 25 shows that with a probe at the same current level as the masker the overlap can be around 100% if both masker and probe are presented at the same electrode. If the masker current level is below the probe current level the overlap can be maximally the neurons activated by the masker when electrodes under the activation region of the probe are chosen.

Figure 26:
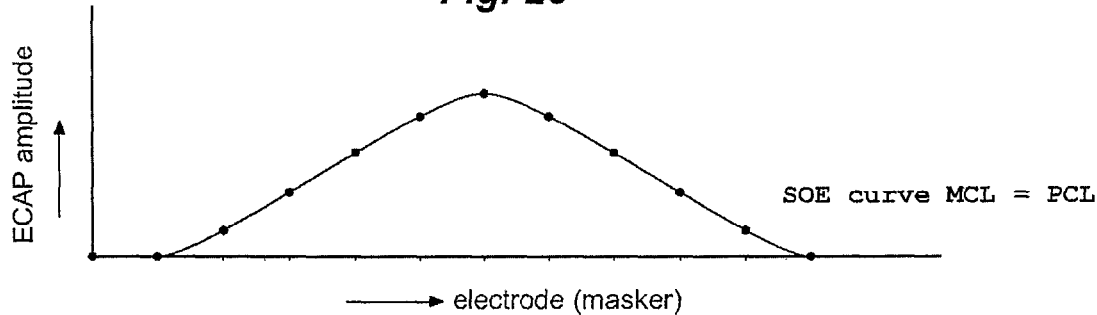
FIG. 26 shows an SOE/ECAP curve obtained with a masker current level=probe current level. Typically a peak in the SOE function is observed.

FIG. 26 shows an SOE/ECAP curve obtained with a masker current level=probe current level with the ECAP amplitude along the y-axis and the masker electrodes along the x-axis.

Figure 27:
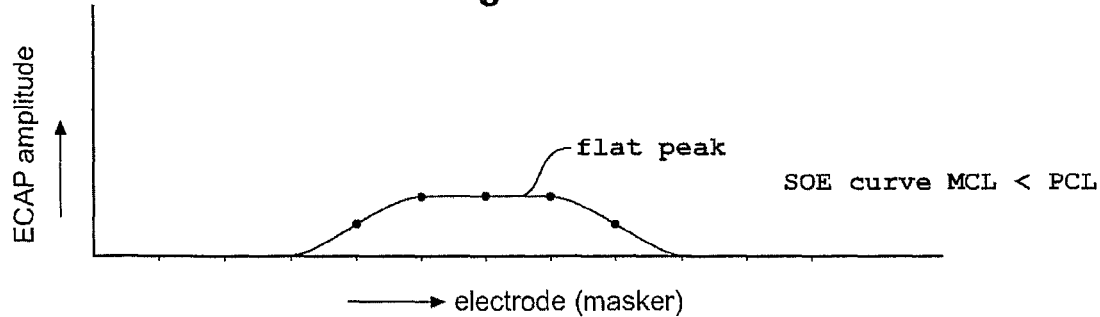
FIG. 27 shows an SOE/ECAP curve obtained with a masker current level<probe current level. These measurements show typically a flattened peak.
Figure 28:
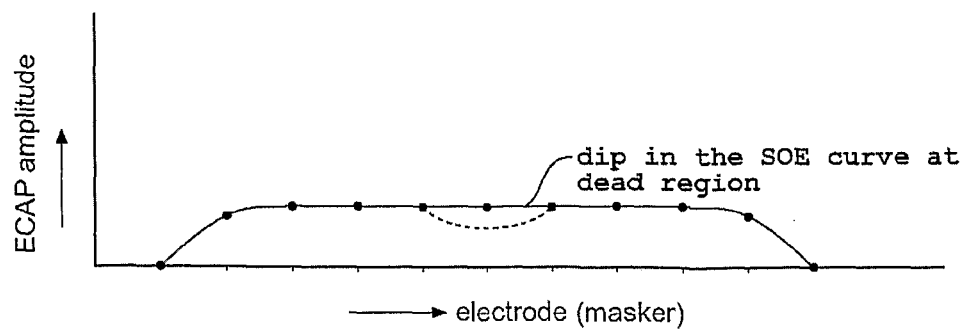
FIG. 28 shows an SOE/ECAP curve with masker current level<probe current.

FIG. 27 shows an SOE/ECAP curve obtained with a masker current level<probe current level with the ECAP amplitude along the y-axis and the masker electrodes along the x-axis. Note that the peak of the SOE/NRT curve becomes flat. If there are dead regions of neurons there is a dip in the flat part of the SOE curve and this is illustrated in FIG. 28. Ideally the method makes use of high level probes that activate all or large proportions of the spiral ganglion neurons and low level maskers that activate small proportions of neurons. The amount of neurons activated by the probe should be high enough to create an ECAP with an amplitude at least twice the noise level of the recording system. Multiple probes can be applied in close succession to assure that large proportions of neurons are activated. The disadvantage of high level probes is that they will be unacceptably loud, even when presented at a low rate. To overcome this problem measurements can be obtained under anaesthesia, e.g. after insertion of the electrode during surgery.

The slope of the ECAP Amplitude growth functions can be used as an indication for dead or partly dead regions. Steep slopes indicate good nerve survival and shallow slopes are an indication for poor nerve survival.

2. Through Psychophysical Measurements:

This method makes use of the fact that when two electrodes activate the same or nearly the same neural population in the spiral ganglion they will create an identical percept. The method can make use of standard psychophysical test algorithms, e.g. 2 alternatives forced choice test.

The test is started by obtaining psychophysical thresholds, using a psychophysical test algorithm (e.g. counting method) for pulse trains of about 0.5 seconds at a pulse rate of 50 to 500 pulses per second on all available electrodes.

The next psychophysical tests are performed with the pulse trains (test pulse train) and threshold current levels (test threshold current level) obtained in the previous test.

Subjects are asked to indicate whether they hear differences between at least two stimuli presented on different electrodes in a 2 alternatives forced choice test. No differences between two electrodes is an indication that these electrodes possibly can have stimulated a dead region. It can also be an indication of poor central place pitch discrimination.

To further identify whether the poor discrimination on the two electrodes is caused by poor nerve survival close to one of the electrodes a stimulus is created in which the two electrodes are stimulated simultaneously through interleaved pulse trains at a low rate (e.g. 10-50 pulses per second) to assure that no adaptation occurs during consecutive presentation of the pulses. The delay between the start of the two interleaved pulse trains is about 250 microseconds, such that the pulses of the second pulse train fall within the absolute refractory period of the first pulse train. If the subject can discriminate the combined pulse trains from the single pulse trains, this indicates a living region. If the subject cannot discriminate the combined pulse train from the single pulse train, this indicates a dead region or an overlapping excitation field of both electrodes which is an indication to consider deactivation of one of the two electrodes of the array.

Figure 29:
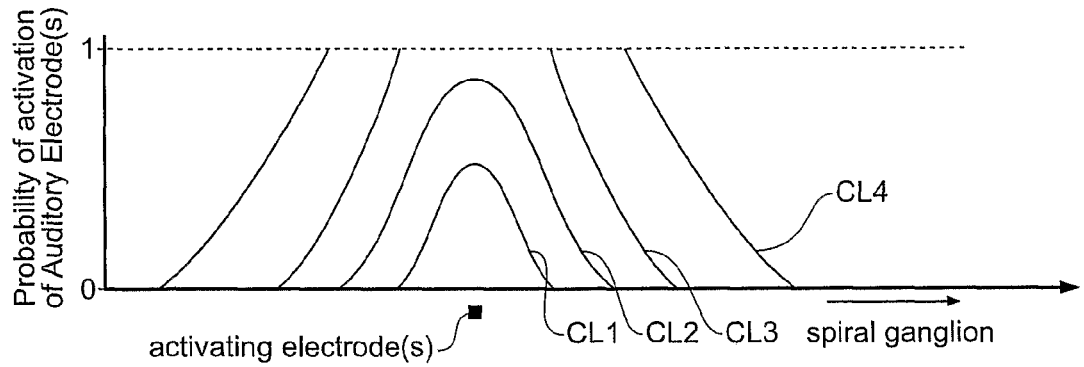
FIG. 29 shows a graph of probability of excitation of auditory neurons along the spiral ganglion.

A further method is described now with reference to FIGS. 29 to 35. In FIG. 29, the horizontal axis represents the spiral ganglion and the shows the probability that neurons in the vicinity of an electrode fire at 4 increasing current levels (CL1, CL2, CL3 and CL4). An activation probability of 1 indicates that all spiral ganglion neurons in proximity are firing and a value below 1 indicates that neurons in that region of the spiral ganglion have a probability of firing and are not always firing. It can be seen that at CL3 and CL4 the probability of spiral ganglion neurons in the vicinity of the activating electrode reach a value of 1, indicating that they are always firing.

At CL 1 and 2 the probability of spiral ganglion firing has not yet reached the plateau and there is a probability of firing of the neurons participating in the Electrically Evoked Compound Action Potential (ECAP).

Figure 30:
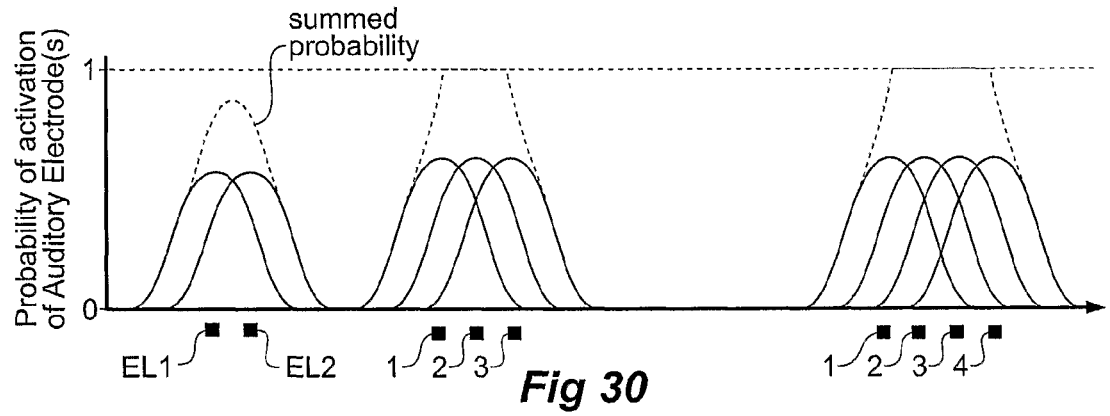
FIG. 30 shows that activation at adjacent sites can be used to reach a probability of 1 at the middle electrode.

FIG. 30 shows that activation at adjacent sites can be used to reach a probability of 1 at the middle electrode.

Figure 31:
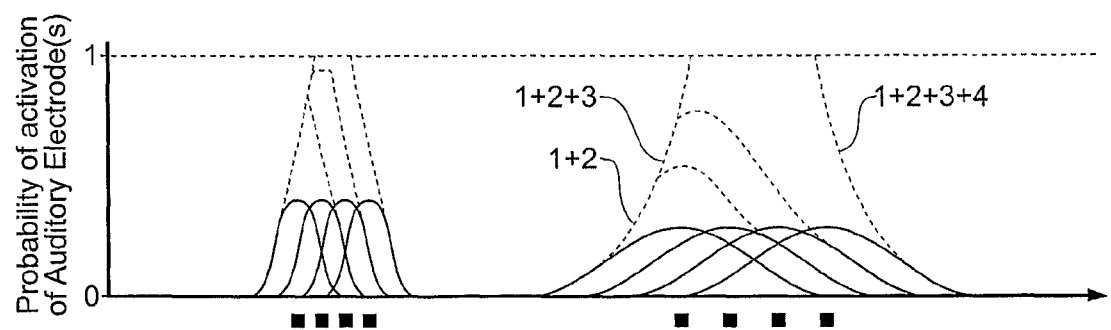
FIG. 31 shows probability curves for 4 active electrodes with focused and broad excitation fields induced by a stimulus.

FIG. 31 shows probability curves for 4 active electrodes with focused (left) and broad (right) excitation fields induced by a stimulus.

Figure 32:
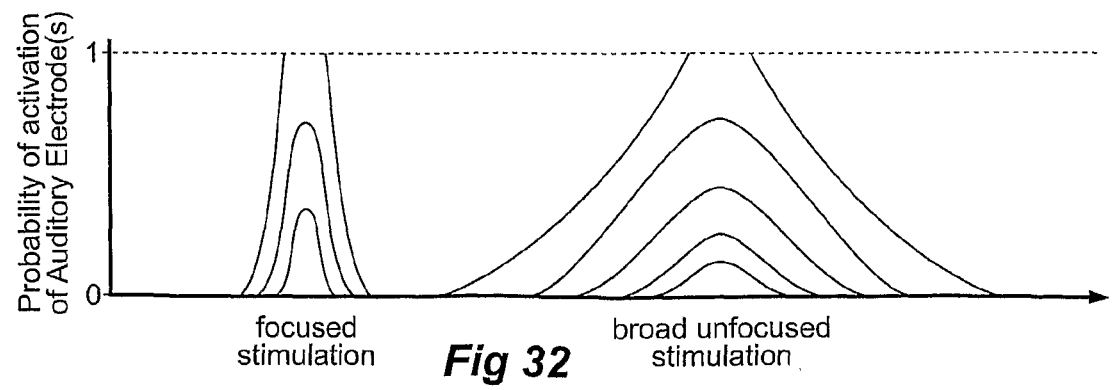
FIG. 32 shows the excitation fields at a range of increasing Current Levels for broad and focused stimulation.

FIG. 32 shows the excitation fields at a range of increasing Current Levels for broad and focused stimulation. It can be seen that with focused stimulation, a probability of 1 is reached with relatively smaller current fields.

As previously described, when using SOE/NRT, a focused masker and a broad probe can be used. If the SOE curves show a peak the probe is not activating a linear portion of the spiral ganglion probability can go beyond 1 by activation of axons in the modiolus regions (although unlikely).

New measurements may be made to identify dead regions as an expansion of the SOE measurement. In one aspect, the principle is to use maskers on multiple electrodes by stimulating them simultaneously or in close succession to ensure that all neurons activated by the probe are in refractoriness.

The measurements may be done under anesthesia to reduce discomfort to the recipient with high level maskers that assure that the probability of 1 has been reached by the neurons close to that electrode. However in conscious subjects the maximum stimulation levels are limited to the loudest acceptable stimulation levels. One solution is to use maskers at a lower level on multiple electrodes (2 or more) and keep the probe close to the middle of these electrodes to ensure that all spiral ganglion neurons are in complete refractoriness for the probe.

By use of this method the masker current levels can be kept at or below probe level and a probe response can be measured at a relatively higher current level as the masker current level determines the highest usable current level. Summation effects might be expected from the use of multiple maskers but these will spread over a shorter range of spiral ganglion cells as occurs with high masker current levels, which is even more applicable to broadly stimulating current fields.

Figure 33:
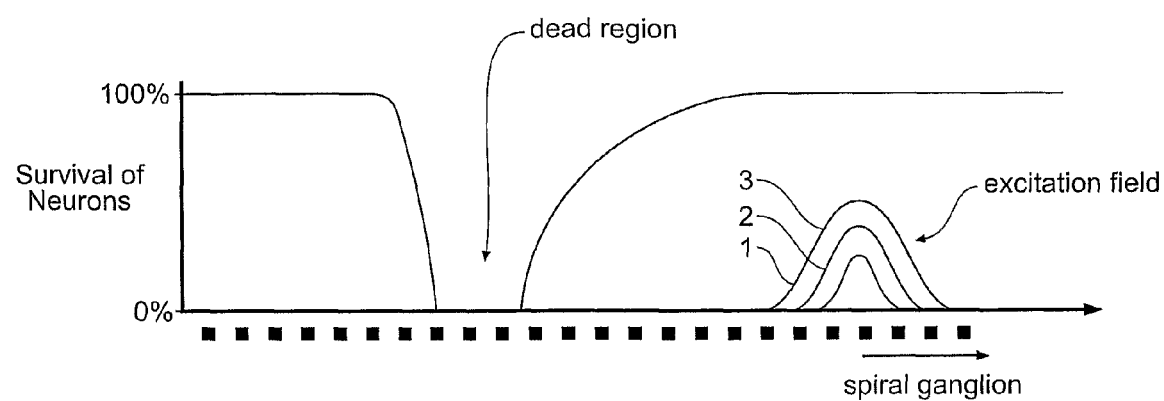
FIG. 33 shows percentage of living neurons across the spiral ganglion.
Figure 34:
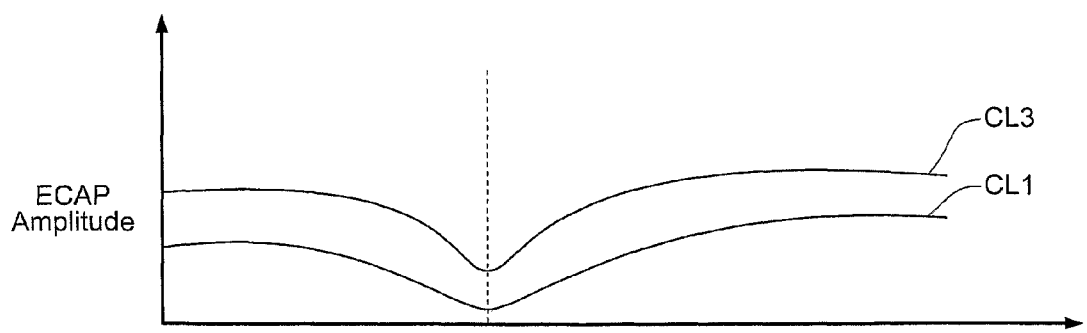
FIG. 34 shows corresponding ECAP measurements for two different current levels of FIG. 33, showing dips at the location of a dead region.

FIGS. 33 and 34 show the application of the new dead region measurements described above. In this application, action potentials are recorded at different current levels. The model assumes that the spiral ganglion is linear over its length. FIG. 33 shows the nerve survival and activation fields evoked by a stimulus at different current levels. A dead region is indicated. When ECAP amplitudes are obtained at different current levels a clear dip in the response amplitudes is observed in the partially and completely dead region as shown in FIG. 34.

Figure 35:
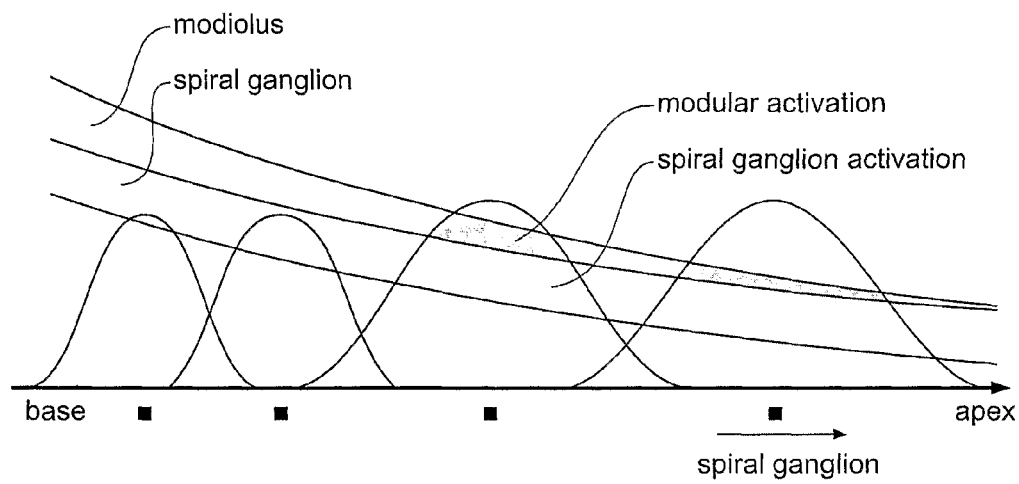
FIG. 35 shows that the electrodes can be at different positions with respect to the neurons that they activate.

FIG. 35 shows that the electrodes can be at different positions with respect to the neurons that they activate. For example, the distance to the modiolus can vary and the modiolar bony wall resistance can vary. Also the density and properties of the modiolar neurons can vary along the spiral ganglion. Based on this model the ECAP amplitudes evoked by a constant current pulse on electrodes placed along the cochlea can vary even if the spiral ganglion contains no dead regions. FIG. 35 also indicates that possibly modiolar activation can be involved at higher current levels.

Figure 36:
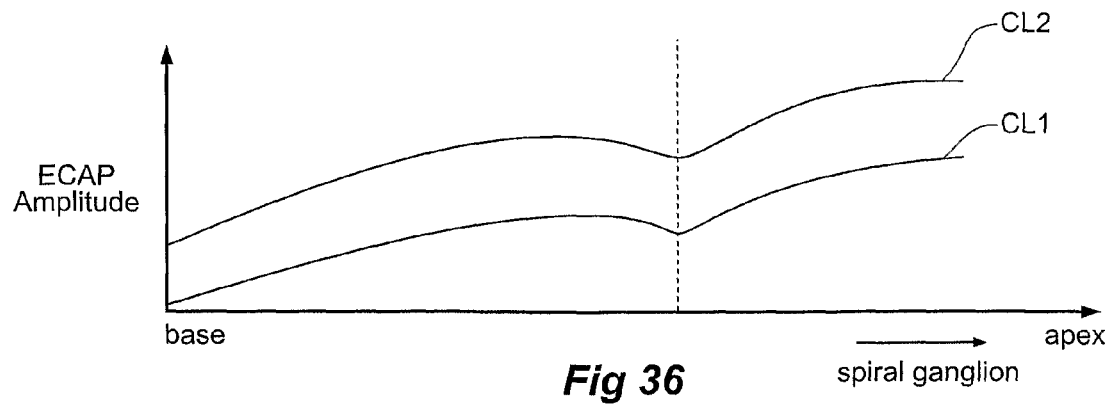
FIG. 36 shows a graph of ECAP amplitude along the spiral ganglion.

It is expected that the change in ECAP amplitudes in a completely living spiral ganglion follows more or less a linear curve. Downward dips in such a curve (see FIG. 36) can be identified as dead regions. The shapes of the curves in relation to normal spiral ganglion survival can be based on analysis of a population (e.g. children with sensory deafness or adults with acute deafness with minimal neural degeneration)

Excitability Model

Thus we have a basis for an excitability model which is to track the proportion of excitable neurons close to the stimulation electrodes. The proportion of excitable neurons (0 to 1) is used to weight the spectral powers of the frequency bands allocated to the electrodes before maxima selection. This effectively controls the stimulation rates of the electrodes in the array. The Excitability Model makes use of several arrays for each electrode to calculate and track the actual proportion of neurons refractory to stimulation.

1. One set of arrays keeps track of the Recovery Functions of the neuronal proportions activated in the past and sums them to calculate the proportion of excitable neurons. A value of 1 indicates complete recovery of local neurons and a value of 0 indicates that all neurons are in refractoriness. The proportion of excited neurons sets the value of the "Plateau Phase" at the start of a Recovery Functions that is followed in real time until the Plateau Phase is reached.
   a. The model predicts activity of neurons and mimics the oscillatory behaviour of ECAP recordings during pulse trains at different rates.
2. The Spread of Excitation function arrays are used to set the proportion of the excitable neurons activated along the electrode array by a stimulus. The aim is to minimize the excitation fields with near threshold stimulus levels and stimulation modes evoking focussed activation fields. Near threshold levels might still evoke a spread activation field and the Spread of Excitation functions are incorporated into the Excitability Model to calculate the excitable proportions for weighting of the spectral powers.
   a. In principle the maximum proportion of excitable neurons allocated to an electrode is 1.
   b. Spread of Excitation can be sharply peaked or have a broad maximum along the electrode array. The peak can be 1 or below 1. Broad peaks indicate that proportions of neurons allocated to nearby electrodes are activated.
   c. Broad Spread of Excitation functions will bring the overall stimulation rate down by exciting populations of neurons of neighbouring electrodes.
   d. Broadly spreading excitation functions will minimize the frequency resolution and smooth the spectral peaks transmitted to the auditory system. These cochlear implant recipients may benefit from lower overall rates and more dispersed activation by broadening of the Spread of Excitation function.
3. Dead regions in the vicinity of an electrode cannot be activated and electrodes allocated to dead regions can be deactivated or the excitability of these sites can be set to 0.

Excitability Controlled Coding of Stimulation

Figure 23:
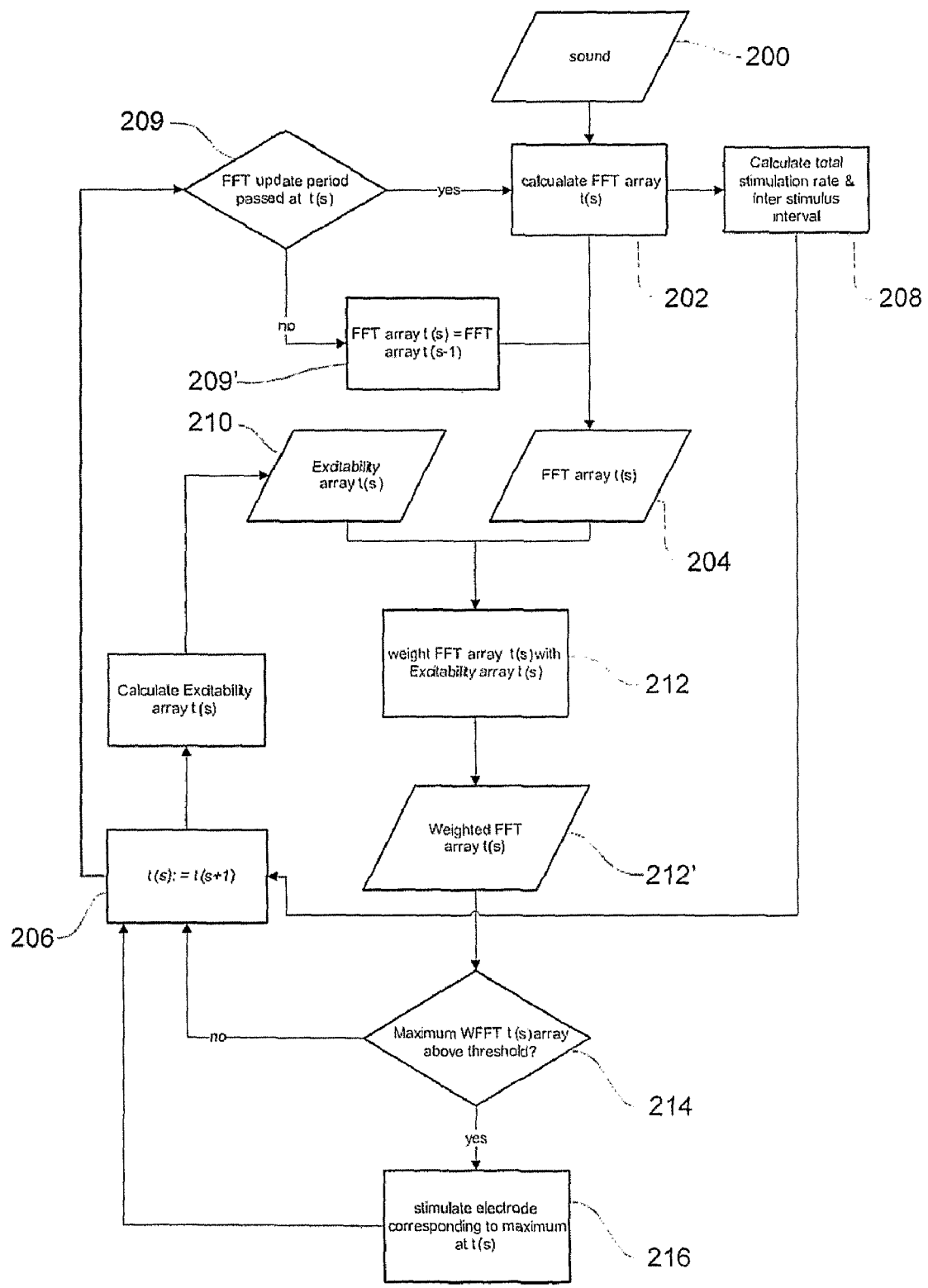
FIG. 23 depicts the steps of the process of applying the relevant functions to the determination of the amount and rate of charging to be applied to each electrode in an array of implanted electrodes.
Figure 24:
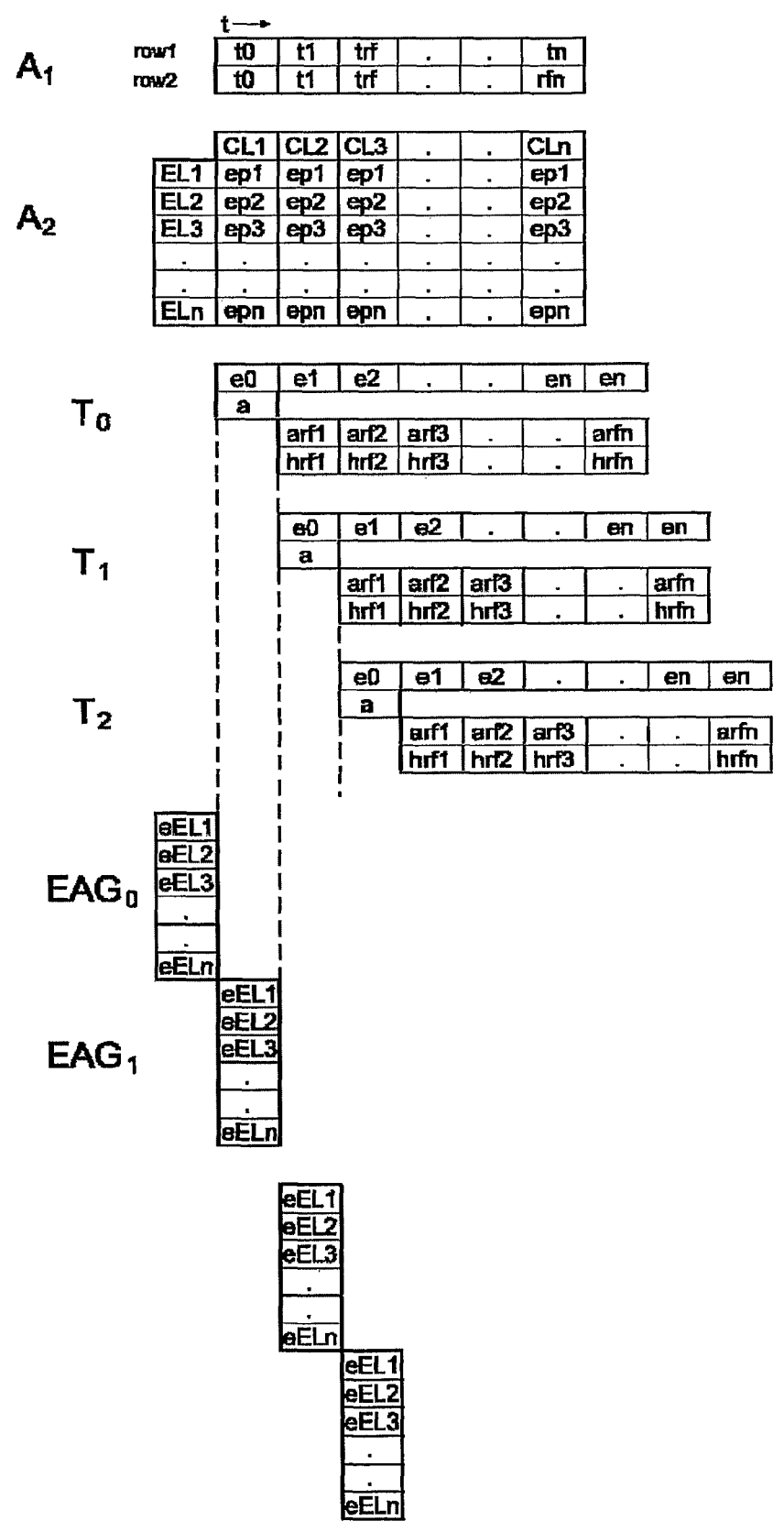

An illustrative model of the Excitability Controlled Coding strategy is described in FIG. 23 and FIG. 24.

The flowchart in FIG. 23 depicts the steps of the process of applying the relevant functions to the determination of the amount and rate of charging to be applied to each electrode in an array of implanted electrodes.

200 The Fast Fourier Transform array "FFT array" is calculated based on the incoming sound. It contains the powers of the filter bands allocated to the electrodes of the stimulation array (=Frequency MAP).

202 The n in the array is equal to the number of bands in the FFT which is equal to the number of electrodes available in the cochlear implant electrode array 204 t(s)=the time that a stimulus can be generated 206 t(s+1)=the next time that a stimulus can be generated 208 The total stimulation rate is calculated based on the powers in the FFT and the interval between stimuli (=1/total stimulus rate) is used to determine the timing of the next stimulus (206)

209 The FFT array (204) used for weighting by the excitability array (210) has not changed if the next stimulus occurs before the FFT update period has passed. A new FFT array is calculated (202) and passed to 204 if the next stimulus occurs after the FFT update period and passed.

The FFT update rate will be slower that the stimulus update rate and the "FFT array" is only calculated if the FFT update period has passed for the planned stimulus.

210 The n in the "Excitability array" is equal to the number of electrodes available in the cochlear implant electrode array and the "Excitability array" is calculated based on the recovery status (see the Calculation of Excitability array depicted in FIG. 24)

212 The "Weighted FFT array" 212' (WFFT) is calculated by multiplying the "FFT array" (204) with the "Excitability array" (210).

216 A stimulus is generated if the WFFT array contains a value above threshold 214.

The calculation and resetting of the stimulation rate based on the total power in the spectrum (208) allows for a smooth occurrence and planning of stimuli over time. When the total stimulation rate is fixed and set too high stimuli would tend to occur in bursts along the whole array, particularly at the onset of sound.

For calculation of the "Excitability array" the highest possible stimulation rate is used but only the "Excitability array" for a planned stimulus is passed to calculate a weighted FFT.

FIG. 24 depicts a model used to calculate the excitability of the neurons associated with an electrode array. Note that the n's used in these tables are variable, e.g. the n in the rfn is different than the n in the ELn.

Referring to array A1 each electrode 1–n has an associated recovery function rf1-rfn.

The topmost row (first row) of array A1 depicts time; the intervals are the shortest possible stimulation periods, at t0 a stimulus is applied to a certain electrode. The second row depicts the beginnings of an array and the row contains the recovery function for the electrode, at rf0 the stimulus is given and at rfn the "plateau recovery time" has been reached. The table can be further expanded by including different recovery functions for the available n electrodes and the n current levels used during stimulation. For simplicity these arrays are not depicted in this figure.

Referring to array A2 for each electrode 1–n the Spread Of Excitation Functions are given by the proportions of neurons excited (ep . . . ) by a given current level (CL . . . ). For each electrode the excitability is tracked into the future based on proportional activation (=excitation) and recovery from excitation; the examples shows the calculation for one electrode as time advances from t0 to t1 and t2.

Calculation of Arrays at t0

The first row of the t0 array shows an array with the "excitable proportions" e0 . . . en corresponding to time t0 . . . tn. Before the start of stimulation all neurons are excitable and this array is filled with proportions: 1,1,1, . . . 1's.

The value "a" indicates the total proportion of neurons activated (=excited) by a stimulus at t0 ["a"="proportion of excitable neurons available at t0 e0)"×"proportion of neurons activated by the stimulus at a given electrode and current level (=ep'x' obtained from the Spread of Excitation array)"]; note that a stimulus can activate proportions of neurons allocated to several electrodes according to the "Spread Of Excitation function" array.

The arf1 . . . arfn array contains the recovery of the activated proportion of neurons over time [=proportion of activated neurons ('a')×the recovery function allocated to the electrode (rf1 . . . rfn)].

The hrf1 . . . hrfn array contains the proportions of neurons recovering from historical activation values are calculated by subtracting the activated proportion ("a") from the proportion available for activation ["hrf1 . . . hrfn"="the proportion available for activation (e1 . . . en)"–"the proportion activated ('a')"].

Calculation of Arrays at t1

At t1 the "excitable proportions" array e0 . . . en contains the proportion of neurons allocated to the electrodes that become excitable over time ["e0 . . . en" ="neurons recovering from historically activation at t0 (hrf1 . . . hrfn)"+"the recovering neurons activated at t0 (arf1 . . . arfn)"] The "a" value, the "arf array" and the "hrf array" are calculated as indicated for t0.

Calculation of Arrays at t2 and Beyond

The t2 array shows the same as the t1 array but advanced in time one period and subsequent arrays have the same configuration as in t1. Note that each time a stimulus is given the timing is started again at t0, etc.

The Excitability Array used for weighting of the FFT (eEL . . . eELn) has a length that is equal to the number of active electrodes (EL) as shown for each time period; at the beginning of stimulation this array is filled with [1,1,1__1]; the values of this array are taken from the excitability calculations for each electrode by obtaining the e0. Excitability Arrays EAt0 and EAt1 are shown for times t0 and t1.

The Activation arrays can be used to get an impression of the temporally evoked activity along the spiral ganglion. These arrays can be filled with the activation values ("a") of the corresponding electrodes at the different points in time. The activation arrays can be used as a model of the effects of the stimulation and can be a useful tool for optimization of the coding strategy and eventually the fitting process.

It should be clear that the calculations described above are an example implementation of coding based on calculations of local excitability. In a real time processor the calculations can be replaced by more complex interacting formulas. E.g.: The recovery function can partly be described by an exponential function and the spread of excitation function can be described by a Gaussian function.

Further Enhancements of the Excitability Controlled Coding Strategy

Other features that can be incorporated into the strategy disclosed herein include without limitation: An Excitability Controlled Coding strategy can be further enhanced by incorporation of "Spontaneous Activity", "Onset and Offset Response" and "Fine Timing" as known from the neurophysiology of the auditory nerve that are useable with the scheme disclosed herein and which also include peak detection and emphasis algorithms and other pre-processing strategies like ADRO, BEAM formers, spectral compression algorithms and statistical analysis of the spectrum etc.

Spontaneous Activity is implemented through random low rate (about 50 pulses per second) stimulation along the electrode array. It is expected that the implementation of spontaneous activity will be more effective for electrode arrays with high number of electrodes (>20 electrodes) as these electrodes will allow the creation of more dispersed stochastic activity along the cochlea. This type of activity is useful for the development of the neurons present in the peripheral and central auditory pathway. Mimicking of the physiological spontaneous activity along the spiral ganglion is expected to at least partly suppress the peripheral and central neural remodelling that occurs when parts of the cochlea do not receive input through their sensory hair cells and thereby prevent or suppress the tinnitus that often occurs in patients with sensorineural deafness.

1. Spontaneous activity should not be heard by the recipient.
2. To assure that stimulation is not heard the lowest possible stimulation levels should be used. These levels can be found by obtaining stimulation thresholds for high rate pulse trains Onset and Offset Response at start and finish of a stimulus is a consideration.

In the normal hearing ear the neurons show an onset and offset response at the start and finish of a stimulus. This temporal response can be emphasized in the coding strategy to better mimic the natural behaviour of auditory neurons to acoustic stimulation.

1. A stimulus Onset Response is detected by a sudden transient increase in the power of a spectral band and implemented by
   a. A short high rate burst at start of the transient.
      1. the burst can be two or more sequential stimuli within a short interval (350 microseconds) where the second pulse is creating a summation effect as also seen in the NRT measurements of a recovery function. The shorter the interval the larger the effect.
   b. An increased stimulation level at start of the transient
2. A stimulus Offset response is detected by a sudden transient disappearance of a high spectral power of a spectral band and implemented by:
   a. A short suppression (5-15 ms) of spontaneous activity at the disappearance of a high spectral power in a spectral band Fine Timing of the stimulation patterns can be implemented based on fine time structure analysis of the frequency spectrum.

1. The weighting can be adapted by phase information to mimic the phased ON/OFF concept of the inner hair cells. This is particularly relevant for the lower frequency channels but can also be applied to higher frequencies. The weighting and thereby the timing of the stimuli can be based on the phase of the centre frequency of the band. For example, the stimulus is preferably delivered during the a predefined phase of the analysed frequency: for example: the positive phase, the negative phase, the phase with positive slopes, the phase with negative slopes, the positive peak, the negative peak, the 0 crossings.
2. Fine timing can be controlled by a applying a weighting to the spectrum in line with the travelling wave model of the acoustically stimulated cochlea.
3. Fine timing can be used for coding of F0. The F0 can be coded through alignment of stimulation within a frame with the F0 period. The concept is to promote focused timing of stimuli around the beginning of this frame to provide additional F0 information to the auditory system. When multiple sound sources are available multiple F0's will be detected. The focus will increase with the statistical power of the main F0. The F0 can be coded by current level modulations. The F0 can be coded by modulation of the stimulation rate.4.

An advanced implementation of the strategy disclosed in this specification includes an emphasis on the spectral peaks in the envelope of the FFT of the received audio signal.

One could include a spectral peak detector and emphasize the peaks in the spectrum by giving them a temporal preference for early stimulation during sequentially interleaved stimulation of one 1 or more channels. A channel can be an electrode or a virtual channel.

Peaks can be further emphasized by using short pulse trains (2 or more pulses in close succession for example at a rate of 20 k pulses per second) for stimulation of the spectral peaks only. A further advancement would be to obtain a measure of the steepness of the flanks of the peak and use rate coding of loudness for the steep peaks and current level coding of loudness for the broad peaks. In addition one might consider using variable stimulation modes (e.g. tri-polar, partially tri-polar and mono-polar) and use tri-polar stimulation for the narrow peaks and partially tri-polar and mono-polar stimulation for the broad peaks. The advantage of mixed stimulation modes it that the power needed to stimulate can be optimized and thereby the battery consumption of the system can be optimized.

The proposed coding strategy can be combined with the concept of a "NofM strategy". A "NofM strategy" relates to the use of selected numbers of peaks when N is less in number than M. Where N=number of spectral peaks selected for stimulation, M=number of spectral peaks in the FFT.

In a conventional strategy, the FFT is divided into a number of spectral bands equal to the number of electrodes in the electrode array. Each electrode equals one pitch.

The steps in a method of implementing a "NofM strategy" are provided by way of example only by the following explanation of the likely steps:

In an NofM (N<M) strategy
   N bands' of the 'FFT array with M bands' are selected for stimulation.
   The N bands are the bands with the highest power. All the other bands will be set to 0 power so they are not stimulated.
   The N bands can also be selected based on the peaks in the "FFT array".
   The M and N bands can contain virtual channels that contain 2 or more nearby electrodes with the highest peaks of a broad peak.
   The N bands can be selected after application of a masking paradigm. After application of a stimulus to a certain electrode, adjacent electrodes can be masked (=not perceivable) for a certain period. It is not effective to stimulate these electrodes and the weighting of the adjacent electrodes is set to 0 for the masked period to avoid that they are picked for stimulation.

It is expected that by use of near threshold stimuli the N in the NofM can be larger than in strategies making use of the full range of current levels. The smaller excitation fields created by near threshold stimuli allow more channels to be stimulated simultaneously using a short sequence without interference compared to the strategies that make use of the high current levels with large excitation fields for coding of loudness. Experiments will have to show what the preferred N is in an NofM "Excitability Controlled Coding" strategy.

The FFT array can be pre-processed by different means for noise suppression, e.g. beam formers, automatic dynamic range optimization. Spectral weightings can be applied to emphasize the bands containing the speech information.

The weighting factors can be adapted by analysis of harmonic information in the spectrum. CI recipients have problems with perceiving harmonics and one might consider doing a fine grained spectral analysis (FFT requiring high levels of processing) and give the higher harmonics a lower power and a lower weighting to avoid confusion or disturb the perception of the most relevant fundamental frequencies.

Virtual Channels

A further strategy can implement what is referred to as virtual channels using the strategy disclosed herein which is different from the way in which fitting are undertaken conventionally. Conventional fitting uses current level settings for coding of loudness. In a conventional strategy a virtual channel is created by the balance of current level on two neighbouring electrodes. In the strategy disclosed in this specification a virtual channel is created by balancing rate on neighbouring electrodes.

Patients can discriminate in virtual channels, i.e. pitches intermediate to the pitches evoked by the individual electrodes when adjacent electrodes are stimulated in short sequence or simultaneously. Virtual channels are a consequence of the overlap of the excitation fields. The intermediate pitches are controlled by balancing of the Current Levels (coding for loudness in conventional strategies) but can also be done by balancing of the stimulation rate (coding of loudness as presented in this disclosure) The intermediate pitches during rate coding are done over time windows of several milliseconds while those created by balancing of the Current Level can be done instantaneously. Most coding strategies include virtual channels automatically by the nature of their coding. Coding strategies can also include virtual channels systematically by expanding the FFT to more bands and stimulating two or more electrodes specifically to create a virtual channel at the peaks in the spectrum.

The use of balanced current levels on adjacent or nearby electrodes (2, two or more) using sequential band/or simultaneous stimulation can provide intermediate pitch percepts between two or more electrodes.

The discrimination of spectral channels by a recipient depends on the number of spectral channels that can be simultaneously processed by their auditory pathway. Minimizing the interference between spectral channels is expected to improve the spectral discrimination of recipients. The number of channels that can simultaneously be processed by recipients is limited to by their interference. Interference is expected to be higher at high current levels.

The disclosed strategy makes use of near threshold stimuli and minimizes the excitation fields evoked by the electrodes. For near threshold stimuli the distance between non-interfering channels (electrode(s)) can be smaller than for stimulation at higher current levels.

The disclosed coding strategy aims to maximize the spectral information delivered to the auditory system through the electrical activation of the spiral ganglion. Temporal channel interaction is minimized by temporally dispersing the activation of the (virtual) channels over the available electrodes. Small excitation fields with near threshold stimuli are used to create minimal overlap between current and excitation field allowing more fine spectral information to be transmitted to the patient.

The effectiveness of virtual channels will increase by coding with near threshold stimuli that allow better pitch resolution along the spiral ganglion through focused stimulation of neural populations close to the electrodes of the perimodiolar intra cochlea electrode array.

The Fitting Process

Having discussed the various refinements that may be applied to the Excitability Controlled Coding strategy it is useful to describe the post fitting processes which desirably provides the basis upon which the coding can be most effectively adapted to a cochlea implant recipient.

Adaption of the ECC strategy makes use of, in this example, mono-polar, bi-polar or tri-polar current pulses, and is performed using the following steps. These steps are described with regard to a specific example, but the generality of the steps can be appreciated from them.

1. Setting the stimulation rate range(s):
   a. The default range of usable rates is expected to be 300 pulses per second (threshold rate) to 1000 pulses per second (comfortable rate). Rate ranges will be CI recipient and electrode specific and the strategy allows for broader or narrower ranges based on individual CI recipient preferences.
   b. The range of rates can be psychophysically obtained by checking for a singular 'tonal' percept during stimulation of one electrode (or channel). The range can be determined by starting with the lowest frequency that gives a tonal percept (lowest rate) at threshold current level and then increasing the rate slowly until the tonal percept starts to change (highest rate). The highest rate can then be put at a comfortable current level and the rate can be decreased until the tonal percept disappears. By this approach overstimulation can be avoided and a first estimate of the current level range that eventually is necessary when not enough loudness can be obtained with rate stimulation alone is determined by the threshold current level for the lowest rate and the comfort current level for the highest rate. The range determinations can be done with continuous sweeps in which the rate is slowly adapted to avoid listening to onset responses. The clinician can stop stimulation if stimulation gets too loud during the rate increase. One can also use half a second pulse trains at different rates and include them in a psychophysical task. Different psychophysical methods (e.g. 2 alternatives as a forced choice) can be used and experiments will show what the typical changes in tonal percepts occur at the borders of the rate range. Audiologists can be trained to look for these effects. E.g. it is known that at rates below 200 pps cochlear implant users tend to hear a galop.
   c. Another approach includes rate and current level for coding of loudness. A range of current levels is distributed over the range of rates that give one tonal percept. Low rates would then use lower current levels than high rates. Further experimental evaluations will determine the optimal methods for determination of stimulation rate and current level ranges.
   d. The stimulation rate ranges along the electrode array are defined by a "Threshold Rate Profile" and a "Comfortable Rate Profile".

2. Setting the current level(s):
   a. One current level per electrode: Preferably only one threshold current level is used for each electrode over a range of stimulation rates. The threshold stimulation level decreases with stimulation rate. For example in one particular implant system the threshold can decrease with 30 Current Levels when stimulation rate is reduces from 500 pulses per second to 1800 pulses per second using a fixed stimulus duration of 500 ms. The aim of the described strategy is to use low rates for soft sound. In order to assure they are audible the "Current Level Thresholds" are obtained at low rates. These thresholds are in the upper part of the dynamic range of high rate stimuli and it is expected they will give a reasonable loudness of the overall MAP in most CI recipients. Thresholds along the electrode array are defined as the "Current Level Threshold Profile". If a CI recipient requires more loudness the "Threshold Current Level Profile" can be shifted to a higher overall current level.
  b. Multiple current levels per electrode: In another approach the current level is an increasing function of stimulation rate. This might be necessary for some CI recipient to create a Map with acceptable loudness. A threshold current level is psychophysically determined for the Threshold Rate and a comfortable current level is determined for the Comfortable Rate used in the MAP. The range of current levels is equally (linearly) distributed along the dynamic stimulation rate range or part of the stimulation rate range. Different distributions, e.g. exponential distributions, of the current level range are possible.
3. Loudness Balancing:
  a. Stimulation is performed at a certain percentage within the dynamic range and the stimulation rate and current level parameters can be adapted to match in loudness along the array.
4. Fitting based on objective measures: (Particularly important for recipients that cannot give direct feedback, e.g. babies or young children or mentally handicapped persons)
  a. ECAP, EABR, Cortical potentials can be used for measurement take during the fitting process.
  b. For example, the ECAP current level threshold profile or an ECAP fixed amplitude profile is obtained through telemetry and then lowered (shifted) until all current levels are well below the expected psychophysical threshold for the lowest stimulation rate (Threshold Rate). The profile is shifted towards higher current levels during continuous random low rate stimulation on all electrodes until a psychophysical threshold is obtained. This current level profile can then be used as a threshold current level profile for the electrode array. Then the clinician can activate the implant and in life mode and present sound at a comfortable level and adapt the dynamic rate range by setting the highest rate that is still comfortable to the recipient. The method can be further adapted and optimized to allow setting of the highest rate. E.g. a rippled spectrum with variable numbers of ripples can be presented and at a comfort level and the dynamic rate range can be increased by increasing the highest rate until the cochlear implant user experiences a change in spectral percept.
5. Fitting can be further fine-tuned by manipulation of current level and stimulation rate profiles. E.g. the profiles can be tilted or a curvature (e.g. U shape or a curvature based on a group of representative patients fitted with an optimal MAP) can be applied to the profile. Also current level and rate settings of individual electrodes can be adapted.
6. Fitting can also be fine-tuned by adapting the rate and current level loudness gain functions of individual electrodes or a range of electrodes.
7. Options to increase the loudness when the MAP is not perceived as adequately loud to the recipient:
  a. Increase threshold current level used to stimulate,
  b. Combine current level and rate range over the input levels,
  c. Increase maximal and/or minimal rate, and/or
  d. Decrease Spread of Excitation.
8. Spread of excitation can be used to optimize the spectral contrast in the MAP. E.g. broad spread of excitation functions in the ECC strategy will cause more spread of activation over the array and puts emphasis on stimulation the electrodes that contain the peaks in the spectrum.

It will also be appreciated that fitting can be based on objective measurements (e.g. ECAP, EABR) and can be used to set threshold profiles, stimulation rate ranges through measurement of recovery functions, spread of excitation functions through ECAP Spread of Excitation functions obtained with NRT and adaptation through measurement adaptation of ECAP responses. These ECAP measurements can be used to feed to the model parameters of the coding strategy disclosed herein during use of the strategy. For example, adaptation and recovery from adaptation can be monitored by measurement of an evoked response to a fixed current level at a fixed interval after the last stimuli in the region of the electrode on which the adaptation is measured. The stimuli used for the measurement of these responses can be included in the random low rate stimulation mimicking spontaneous activity of the coding strategy, they can be based on stimuli evoked by the audio signal received by the microphone of the implant system and they can be started by a trigger of the clinician or implant user. Data can be logged in the implant, the speech processor and a remote system to help with clinical evaluations.

Tinnitus

Most cochlear implant patients perceive a relief or suppression of their tinnitus after successful implantation and use of their implant system. In some subjects the inhibition of the tinnitus occurs only during stimulation while others have the benefits of residual inhibition. Most recipients do not wear their system overnight and residual inhibition at the beginning of the night after disconnection of the external sound processor allows these patients to fall asleep. Some recipients do not experience residual inhibition and they may use their system during falling asleep or keep it on at night. Cochlear implant recipients can use masker sounds to mask their tinnitus. It is expected that with the current coding strategy with improved spectral contrast and enlarged dynamic range more natural (e.g. waterfall) and acceptable masker stimuli can be created. The implant system can include implantable batteries to allow stimulation overnight. The recipient can choose and select a night program through their Behind The Ear BTE and/or Remote System. The night program can be a free running coding strategy coding the sound picked up by the BTE processor, a remote acoustical processor [e.g. external Wireless Assistant (WA)] that transmits the code to a Coil processor through for instance Bluetooth. The coil can be attached to the head in several ways; e.g. a headband or a hat. The coil can also be hidden in the pillow or mattress.

The BTE of a CI can be made smaller by use of an external WA that transmits the coded sound to the coil while the coil is dedicated to decoding of the received code from the WA and transmits the coded RF to the internal system. The system can include a separate set of microphones that can be attached to the recipient in several ways and transmits the sound to the WA for coding. Future CI systems include implantable batteries (e.g. totally implantable Cochlear Implant system). The implanted battery can be used to help patients that are bothered by tinnitus at night.

At the start of the night the recipient can choose to put on a relaxing masker stimulus that does not rely on external input and is stored on the memory implanted in the implant. Music appreciation is disappointing for most cochlear implant recipients. It is expected that with the current coding approach more natural sound can be created that will allow for more natural tinnitus maskers that are more acceptable to implant recipients.

The disclosed strategy can be adapted for night use and include spontaneous firing (low rate and/or high rate random stimulation) and a limited dynamic range, as disclosed previously.

Use of rate for loudness coding and focused stimulation using multi-electrode intra cochlear electrode arrays, making use of physiological models for implementation of stimulation is disclosed herein.

It will be appreciated that a variety of pulses and pulse bursts can be used. Furthermore as higher stimulation rates have lower thresholds one could obtain the threshold current level at a higher rate; e.g. 250 pps and then use the same current level for random stimulation at a lower rate e.g. 50 pps. This can provide for neural stimulation occurring at a level below threshold level.

It is expected that the disclosed coding strategy based on neurophysiological modeling will better mimic normal hearing in cochlear implant recipients and thereby also improve the suppression and prevention of tinnitus. Furthermore it is expected that part of the tinnitus suppression effect is related to masking of the perceived tinnitus sound by the sound transposed through electrical stimulation to the auditory nerve. It is known that the quality of sound is impaired and often poor in cochlear implant users. Therefore it is difficult to create masker stimuli that are acceptable for continuous use by recipients. The disclosed coding strategy will allow creation of more natural sound percepts and thereby more natural masker stimuli (e.g. those resembling a waterfall sound) that will be more acceptable for continuous use to cochlear implant recipients with tinnitus problems.

In the normal developing ear the spontaneous activity is involved in the development of the peripheral and central auditory system. In subjects with complete or partial sensory deafness there is no spontaneous activity of the auditory nerve and the peripheral and the central auditory system is remodeled which can lead to tinnitus. By mimicking the natural auditory neuron activity (both spontaneous activity and sound evoked activity) the neural system the remodeling will be stopped or reverted and thereby the tinnitus will be prevented or suppressed.

The tinnitus maskers or spontaneous activity can be provided without external processor though cochlear implants that contain a battery, a signal processor and memory. The patient can activate and deactivate the tinnitus masking modes through the external processor and then leave the implant functioning by itself. The stand alone mode of the implant is particularly useful at times when the recipients does not need sound input, e.g. during falling asleep or sleep. The tinnitus masker signals can also be provided through an external processor.

Cochlear implant system with tinnitus suppression mode can be beneficial for patients with severe tinnitus that have residual hearing in the ipsi- and/or contralateral ear, particularly when the implanted electrode is able to preserve the residual hearing of the recipient.

The strategy disclosed in this specification is particularly suitable for electrode arrays with multiple perimodiolar electrodes. It is expected that electrode arrays will contain more electrodes in the future and this strategy is expected to make effective use of these electrodes and it is expected that the performance will increase with the number of electrodes available.

However, currently used implant technology can be used to implement the strategy disclosed.

There is a chance that battery consumption in associated implant apparatus can be lowered compared to current apparatus, as lowest applicable pulse rates are used and a lower supply voltage can be used to stimulate electrodes when using near threshold stimuli.

It will be apparent that numerous types of pulses may be used as appropriate, as will be appreciated by the person skilled in the art. Various pulse types are illustrated in FIGS. 37a to 37d. For example, in one form, the pulses are charge balanced and can be biphasic symmetrical current pulses with an inter-phase-gap (FIG. 37a), asymmetrical biphasic current pulses (FIG. 37b), triphasic current pulses including a variety of phase durations (FIG. 37c) or pulses containing more than 3 phases (for example 7 phases, as shown in FIG. 37d).

A further aspect of the present invention also provides for a signal processor and/or associated cochlear implant system which is configured to carry out the various methods described herein.

Also contemplated is a machine readable medium containing instructions thereon to cause a machine, such as a computer or other data processor, to carry out the steps of the various methods described herein. Such a medium could include a memory device such a computer hard drive, a dvd, a ed, a memory on a microprocessor, a hologram or any other suitable type of machine readable memory.

It will also be appreciated that the various aspects of the present invention may be used in various types of cochlear implants including partially implantable as well as totally implantable. The various aspects may also be applied to other medical implants such as ABI (Auditory Brainstem Implant, electrode for hearing, placed in the brainstem) such as Cochlear Corporation's Nucleus 24 [R] Multichannel Auditory Brainstem Implant (Multichannel ABI)

It will be appreciated by those skilled in the art that the present invention is not restricted to the embodiment described herein and also not in regard to the particular elements and/or features described or depicted herein. It will be appreciated that various modifications can be made without departing from the principles of the invention. Therefore, the invention should be understood to include all such modifications within its scope.

The invention claimed is:

1. A method for delivering a stimulation by a cochlear implant having a plurality of electrodes, comprising:
    receiving a sound signal;
    filtering the received sound signal to obtain a set of one or more band limited signals each corresponding to a particular frequency band;
    applying a weight to at least one of the band limited signals to obtain at least one weighted signal, wherein the applied weight is determined using a function of an excitability of neurons in a vicinity of at least one electrode of the plurality of electrodes corresponding to the frequency band of the band limited signal;
    selecting a signal from amongst the at least one weighted signal;
    generating a stimulation signal based on the selected signal; and
    delivering the stimulation signal via at least one of the electrodes.

2. The method of claim 1, wherein the function of the excitability of neurons is determined using a spread of excitation function.

3. The method of claim 2, further comprising:
measuring the spread of excitation function by measuring electrically evoked compound action potentials (ECAPs) using the plurality of electrodes of the cochlear implant.

4. The method of claim 1, wherein the function of a excitability of neurons is further determined using an auditory neuron recovery function.

5. The method of claim 4, further comprising:
measuring the auditory neuron recovery function by measuring electrically evoked compound action potentials (ECAPs) using the plurality of electrodes of the cochlear implant.

6. The method of claim 4, wherein the function of the excitability of neurons is further determined using an adaptation function.

7. The method of claim 6, further comprising:
modifying the auditory neuron recovery function using the adaptation function.

8. The method of claim 1, wherein selecting a signal comprises selecting a maxima.

9. The method of claim 1, wherein obtaining a first set of one or more band limited signals comprises:
applying a fast Fourier transform (FFT) to the received sound signal to obtain a first set of one or more frequency band limited signals.

10. The method of claim 1, wherein generating a stimulation signal comprises:
generating a stimulation signal comprising a plurality of pulses, wherein a loudness level of the applied stimulation is controlled by adjusting a rate of application of the pulses.

11. The method of claim 10, wherein the plurality of pulses are at a near threshold current.

12. A cochlear implant comprising:
a microphone;
a plurality of electrodes; and
a signal processor configured to filter a sound signal received from the microphone to obtain a set of one or more band limited signals each corresponding to a particular frequency band, apply a weight to at least one of the band limited signals to obtain at least one weighted signal, wherein the applied weight is determined using a function of an excitability of neurons in a vicinity of at least one electrode of the plurality of electrodes corresponding to the frequency band of the band limited signal, select a signal from amongst the at least one signal, weighted signals, generate a stimulation signal based on the selected signal, and deliver the stimulation signal via at least one of the electrodes.

13. The cochlear implant of claim 12, wherein the function of the excitability of neurons is determined using a spread of excitation function.

14. The cochlear implant of claim 13, wherein the spread of excitation function is obtained by measuring electrically evoked compound action potentials (ECAPs) using the plurality of electrodes of the cochlear implant.

15. The cochlear implant of claim 13, wherein the function of the excitability of neurons is further determined using an auditory neuron recovery function.

16. The cochlear implant of claim 13, wherein the function of the excitability of neurons is further determined using an adaptation function.

17. The cochlear implant of claim 12, wherein the signal processor in selecting a signal is configured to select a maxima.

18. The cochlear implant of claim 12, wherein the signal processor in obtaining a first set of one or more frequency band limited signals is configured to apply a fast Fourier transform (FFT) to the received signal to obtain a first set of one or more frequency band limited signals.

19. The cochlear implant of claim 12, wherein the signal processor in generating a stimulation signal is configured to generate a stimulation signal comprising a plurality of pulses, wherein a loudness level of the applied stimulation is controlled by adjusting a rate of application of the pulses.

20. The cochlear implant of claim 19, wherein the plurality of pulses are at a near threshold current.

* * * * *